(12) United States Patent
Deprez et al.

(10) Patent No.: US 7,605,261 B2
(45) Date of Patent: Oct. 20, 2009

(54) UREA DERIVATIVES, METHOD FOR PREPARING SAME, USE THEREOF AS MEDICINES, PHARMACEUTICAL COMPOSITIONS AND NOVEL USE

(75) Inventors: Pierre Deprez, Thiasis (FR); Marcel Patek, Neratovice (CZ)

(73) Assignee: Amgen Inc., Thousand Oaks, CA (US)

( * ) Notice: Subject to any disclaimer, the term of this patent is extended or adjusted under 35 U.S.C. 154(b) by 42 days.

(21) Appl. No.: 11/644,343

(22) Filed: Dec. 22, 2006

(65) Prior Publication Data
US 2007/0173502 A1  Jul. 26, 2007

Related U.S. Application Data

(63) Continuation of application No. 10/466,571, filed as application No. PCT/FR02/00279 on Jan. 23, 2002, now abandoned.

(30) Foreign Application Priority Data

Jan. 26, 2001 (FR) ................... 01 01054

(51) Int. Cl.
*C07D 295/00* (2006.01)
*C07D 265/30* (2006.01)
*C07D 241/04* (2006.01)
*A61K 31/535* (2006.01)
*A61K 31/497* (2006.01)

(52) U.S. Cl. ............... 544/358; 544/63; 544/98; 544/106; 544/224; 544/336; 514/228.8; 514/231.2; 514/247; 514/252.1; 514/252.12

(58) Field of Classification Search ............ 544/106, 544/336, 63, 98, 224, 358; 514/228.8, 231.2, 514/247, 252.1, 252.12
See application file for complete search history.

(56) References Cited

U.S. PATENT DOCUMENTS 4,521,583 A * 6/1985 Kohli ................. 528/119
5,849,732 A  12/1998 Suzuki et al.

FOREIGN PATENT DOCUMENTS

| JP | 58-109464 | 6/1983 |
|---|---|---|
| JP | 08-041006 | 2/1996 |
| JP | 10-195037 | 7/1998 |
| JP | 11-139969 | 5/1999 |

\* cited by examiner

*Primary Examiner*—Kamal A Saeed
*Assistant Examiner*—Samantha L Shterengarts
(74) *Attorney, Agent, or Firm*—Olga Mekhovich

(57) ABSTRACT

The invention relates to new products of formula (I):

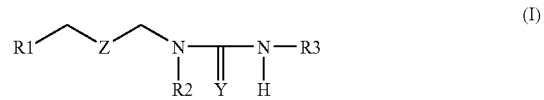

in which:
Y represents oxygen or sulphur,
Z represents C=CH2, CH—CH3 or CH2,
R1 represents hydrogen, morpholinyl or the

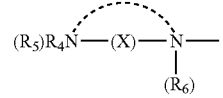

radical. In which the two nitrogen atoms are linear or form a cyclic radical, X represents carbonyl, alkylene or alkenylene, linear or branched, containing at most 6 carbon atoms optionally interrupted by oxygen or sulphur,
R4, R5 and R6 represent hydrogen, a protective group of the nitrogen, alkyl, cycloalkyl, aryl and arylalkyl optionally substituted,
R2 represents alkyl optionally substituted by aryl, heteroaryl or —NR4R5,
R3 represents alkyl, cycloalkyl, aryl, heteroaryl, arylalkyl or heteroarylalkyl optionally substituted,
these products being in all isomer forms and the salts, as medicaments.

23 Claims, 9 Drawing Sheets

(XI)

1a

1b

1c

1d

1e

1f

1g

1h

1i

1j

1k

1l

1m

1n

| N° EX | MH + |
|---|---|
| 1 | 437 + |
| 2 | 465 + |
| 3 | 435 + |
| 4 | 483 + |
| 5 | 485 + |
| 9 | 499 + |
| 10 | 471 + |
| 11 | 489 + |
| 12 | 469 + |
| 6 | 503 + |
| 7 | 513 + |
| 8 | 485 + |
| 13 | 466 + |
| 14 | 494 + |
| 15 | 484 + |
| 16 | 464 + |
| 17 | 466 + |
| 18 | 439 + |
| 19 | 467 + |
| 20 | 437 + |
| 21 | 457 + |
| 22 | 439 + |
| 74 | 375 + |
| 78 | 497 + |
| 76 | 513 + |
| 77 | 541 + |
| 79 | 513 + |
| 80 | 531 + |
| 81 | 511 + |
| 82 | 449 + |
| 75 | 365 + |
| 100 | 501 + |
| 101 | 529 + |
| 102 | 485 + |
| 103 | 501 + |
| 104 | 519 + |
| 105 | 499 + |
| 106 | 437 + |
| 99 | 451.4 + |
| 98 | 513.4 + |
| 97 | 533.3 + |
| 23 | 497 + |

Figure 4

| Structure | N° ex. | MH+ | compounds |
|---|---|---|---|
| 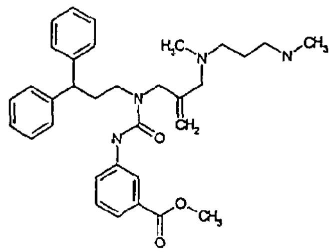 | 107 | 543+ | 1m 2f 3b |
| 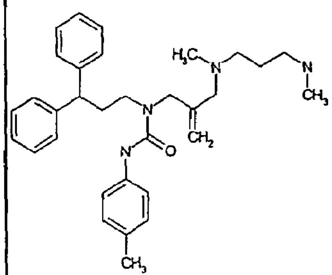 | 108 | 499+ | 1m 2f 3g |
| 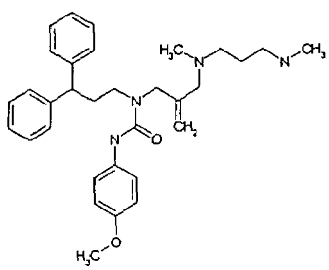 | 109 | 515+ | 1m 2f 3d |
| 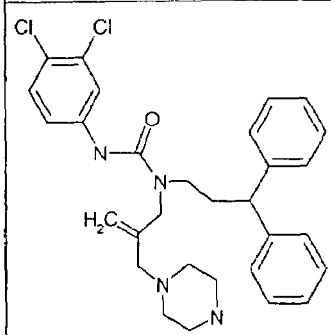 | 110 | 538+ | 1a 2f 3x |
| 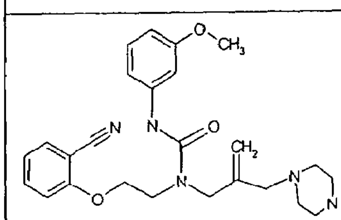 | 111 | 450+ | 1a 2i 3a |

Figure 5a

| Structure | # | Mass | Code |
|---|---|---|---|
| 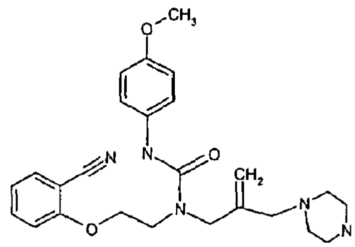 | 112 | 450+ | 1a 2i 3d |
| 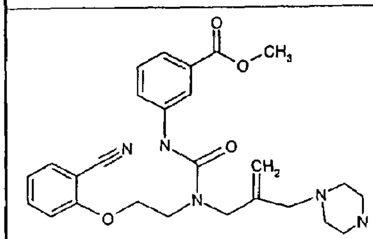 | 113 | 478+ | 1a 2i 3b |
| 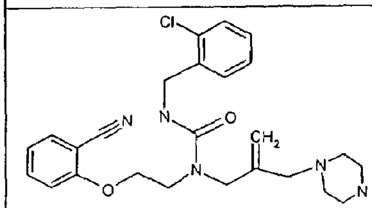 | 114 | 468+ | 1a 2i 3e |
| 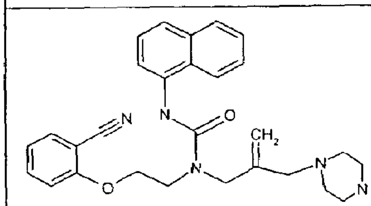 | 115 | 470+ | 1a 2i 3u |
| 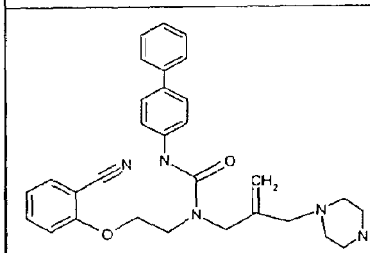 | 116 | 496+ | 1a 2h 3w |
| 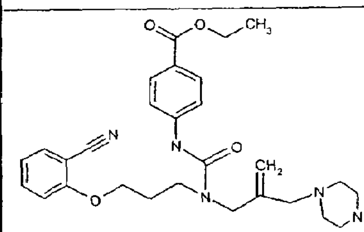 | 117 | 506+ | 1a 2h 3v |
| 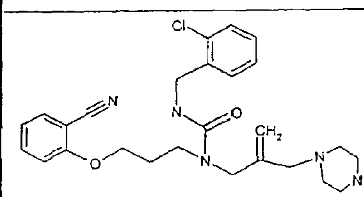 | 118 | 482+ | 1a 2h 3e |

Figure 5b

| Structure | # | MS | Synthesis |
|---|---|---|---|
| 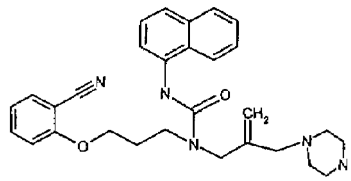 | 119 | 484+ | 1a 2h 3u |
| 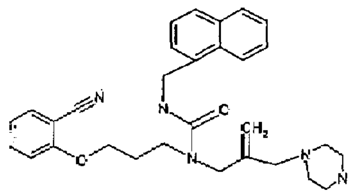 | 120 | 498+ | 1a 2h 3t |
| 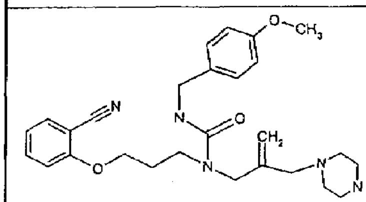 | 121 | 478+ | 1a 2h 3n |
| 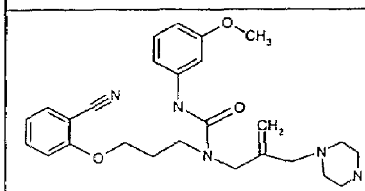 | 122 | 464+ | 1a 2h 3a |
| 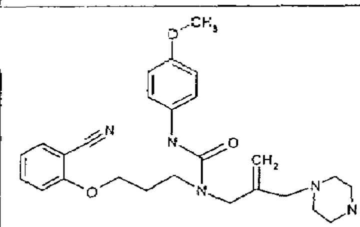 | 123 | 464+ | 1a 2h 3d |
| 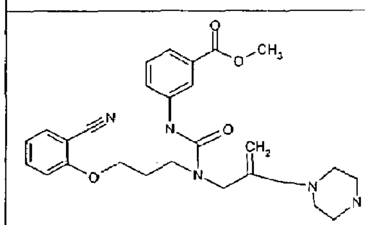 | 124 | 492+ | 1a 2h 3b |
| 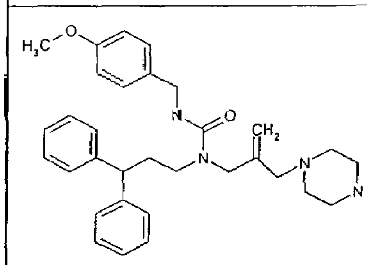 | 125 | M+=513+ | 1a 2f 3n |

| | 126 | M+= 517+ | 1a 2f 3z2 |
|---|---|---|---|
|  | | | |
|  | 127 | 538+ | 1a 2f 3z4 |
|  | 128 | 503+ | 1a 2f 3z3 |
|  | 129 | 545+ | 1a 2f 3z1 |
|  | 130 | 511+ | 1a 2f 3y |

UREA DERIVATIVES, METHOD FOR PREPARING SAME, USE THEREOF AS MEDICINES, PHARMACEUTICAL COMPOSITIONS AND NOVEL USE

CROSS-REFERENCES TO RELATED APPLICATIONS

This application is a continuation of U.S. Ser. No. 10/466,571, filed Sep. 30, 2003, which is a 371 of PCT/FR02/00279 filed on Jan. 23, 2002, which are hereby incorporated by reference.

The present invention relates to new derivatives of urea, their preparation process, the new intermediates obtained, their use as medicaments, the pharmaceutical compositions containing them and the new use of such derivatives of urea. Therefore a subject of the present invention is new derivatives of urea which can have properties allowing them to participate in modulating the activities of inorganic ions acting in particular at the level of receptors of such inorganic ions.

Thus the products of the present Application can act at the level of receptors of inorganic ions and in particular at the level of calcium membrane receptors capable of binding extracellular calcium.

The concentration of extracellular calcium is finely regulated in the organism and one of the actors of this regulation is the calcium receptor called Ca sensing receptor or CaSR. Such a receptor at the surface of certain cells can detect the presence of calcium. Certain cells of the organism do not respond just to chemical signals but also to ions such the extracellular calcium ions ($Ca^{++}$): changes in the concentration of these extracellular $Ca^{++}$ ions can modify the functional responses of these cells. Among these cells, there can be mentioned the parathyroid cells which secrete the parathyroid hormone called PTH. The parathyroid cells therefore have at their surface the Calcium receptor (CaSR) which detects changes in the concentration of extracellular calcium and initiates the functional response of this cell which is a modulation of the secretion of the parathyroid hormone (PTH).

By way of additional information on the Ca receptor (CaSR), the publication Brown et al, 366, Nature, 574, 1993 and also the documents WO 95/11221 and WO 97/37967 can be mentioned. The products of the present invention can thus participate in modulating the secretion of the PTH by acting at the level of ionic receptors in particular CaSR and via the mobilisation of intracellular calcium ions (increase or reduction in the concentration of these ions).

BRIEF DESCRIPTION OF DRAWINGS

FIG. 4 represents a table of analytic MH+ results.

FIG. 5a represents a table of analytic MH+ results.

FIG. 5b represents a table of analytic MH+ results.

Figure 1:
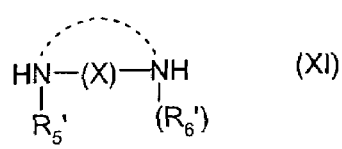
FIG. 1 describes 14 compounds of formula (XI): 1a to 1n.
Figure 1:
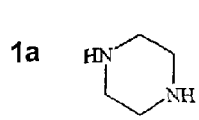
Figure 1:
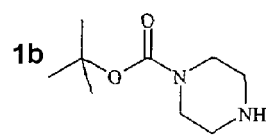
Figure 1:
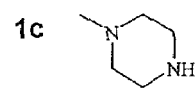
Figure 1:
Figure 1:
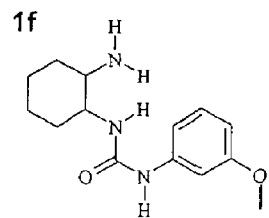
Figure 1:
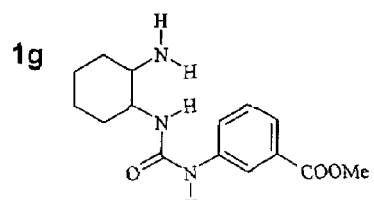
Figure 1:
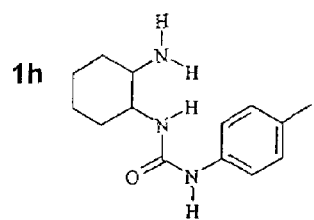
Figure 1:
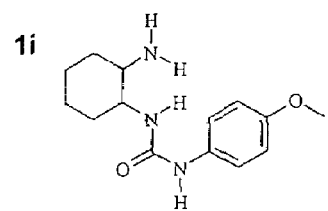
Figure 1:
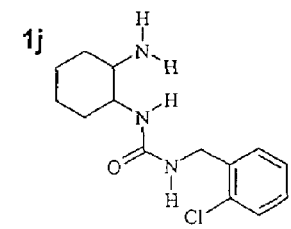
Figure 1:
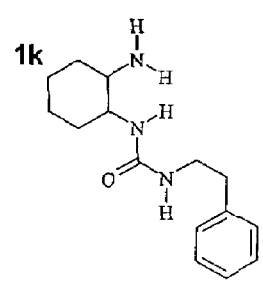
Figure 1:
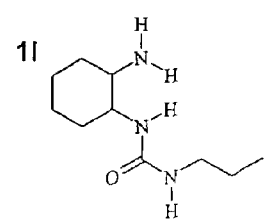
Figure 1:
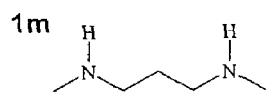
Figure 1:
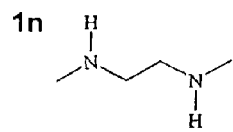
Figure 1:
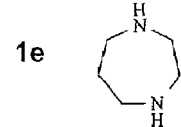

Therefore a subject of the present invention is the products of formula (I):

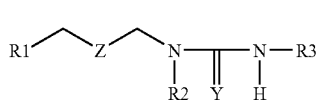

in which:

Y represents the oxygen or sulphur atom,

Z represents the divalent C=CH2, CH—CH3 or CH2 radical,

R1 represents a hydrogen atom, an optionally substituted morpholinyl radical or a diamine radical of formula:

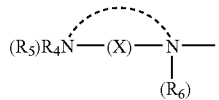

which represents:
either a saturated:

radical
or an unsaturated:

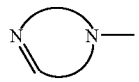

radical
or the;

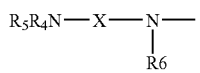

radical
in which the continuous arc indicates that the two nitrogen atoms form a monocyclic heterocyclic saturated or unsaturated optionally substituted radical constituted by at most 8 members, the nitrogen atoms being able to be or not able be consecutive on the ring thus formed, X represents a carbonyl, linear or branched alkylene or alkenylene radical containing at most 6 carbon atoms optionally interrupted by one or more oxygen or sulphur atoms, R4, R5 and R6, identical or different, are chosen from the hydrogen atom, the protective groups of the nitrogen atom, the linear or branched alkyl radicals containing at most 4 carbon atoms, cycloalkyl containing at most 6 members, aryl and arylalkyl radicals, all these alkyl, cycloalkyl, aryl and arylalkyl radicals being themselves optionally substituted, R2 represents a linear or branched alkyl radical containing at most 6 carbon atoms optionally substituted by one or more identical or different radicals chosen from the aryl or heteroaryl radicals themselves optionally substituted and the —NR4R5 radical in which R4 and R5, identical or different, have the meaning indicated above, R3 represents a linear or branched alkyl radical containing at most 6 carbon atoms, cycloalkyl containing at most 12 members, aryl, heteroaryl, arylalkyl or heteroarylalkyl in which the alkyl radical is linear or branched containing at most 4 carbon atoms, all these radicals being optionally substituted, it being understood that all the heterocyclic, morpholinyl, cycloalkyl, alkyl, aryl, heteroaryl, arylalkyl and heteroarylalkyl radicals indicated above as being optionally substituted, are optionally substituted by one or more identical or different radicals chosen from halogen atoms, the hydroxyl, phenyl, phenoxy, trifluoromethyl, trifluoromethoxy, cyano, free, salified or esterified carboxy radicals, the linear or branched alkyl, alkenyl, alkylthio or alkoxy radicals containing at most 4 carbon atoms, the —NR4R5, —NHR4, —COR4, —COOR4 and —CONHR4 radicals in which R4 has the meaning indicated above and the radicals with an acid function and acid isosteres, all the aryl and arylalkyl radicals being moreover optionally substituted by a dioxol radical formed on two consecutive carbon atoms of the aryl radical considered, said products of formula (I) being in all possible racemic, enantiomeric and diastereoisomeric isomer forms, as well as the addition salts with mineral and organic acids or with mineral and organic bases of said products of formula (I).

In the products of formula (I) and in what follows, R1 therefore represents either a hydrogen atom, or an optionally substituted morpholinyl radical or the diamine radical of formula

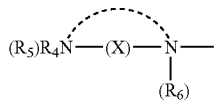

In the above diamine radical:

either the two nitrogen atoms represented together form a saturated ring and R1 is then defined by the substituent R4 and the two nitrogen atoms N, N as follows:

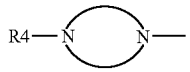

or the two nitrogen atoms represented together form an unsaturated ring in which the nitrogen atom involved in an unsaturated bond no longer comprises the R4 radical: R1 is then defined by an unsaturated ring comprising the two nitrogen atoms N, N as follows:

or the two nitrogen atoms represented together do not form a ring and R1 is then defined by the substituents R4, R5, R6 and X is as follows:

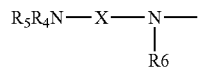

the definitions of the substituents R4, R5, R6 and X being given above.

In the products of formula (I) and in what follows:

the term monocyclic heterocyclic saturated or unsaturated radical constituted by at most 8 members therefore designates a radical containing at least two nitrogen atoms but also optionally containing another nitrogen atom or one or more oxygen or sulphur atoms: such a heterocyclic radical therefore designates a carbocyclic radical interrupted by one or more heteroatoms chosen from oxygen, nitrogen or sulphur atoms, the heteroatoms of these heterocyclic radicals can therefore be identical or different: by way of non-exhaustive examples, there can be mentioned in particular the imidazolyl, pyrazolyl, pyrazinyl, pyrimidinyl, pyridazinyl, furazannyl, imidazolidinyl, delta-2-imidazolinyl, pyrazolidinyl, delta-3-pyrazolinyl, piperazinyl or also homopiperazinyl radical, all these radicals being optionally substituted.

In particular the piperazinyl or homopiperazinyl radicals are optionally substituted by a carboxy or alkyl radical, linear or branched, containing at most 4 carbon atoms.

It should be noted that when R1 represents a monocyclic heterocyclic unsaturated radical as defined above, R1 represents in particular an imidazolyl, pyrazolyl, delta-2-imidazolinyl or also delta-3-pyrazolinyl radical.

It should be noted that when R1 represents a monocyclic heterocyclic saturated radical as defined above, R1 represents in particular an imidazolidinyl, pyrazolidinyl, piperazinyl or also homopiperazinyl radical.

the term protective groups of the nitrogen atom designates the standard protective groups such as in particular those described in the reference: 'Protective groups in organic synthesis' by T. Greene (Ed John Wiley and Sons, inc): there can be mentioned more particularly the esterified carboxy radical in particular terbutoxycarbonyl or (BOC), the benzyl radical or also the phthalimido radical.

the term linear or branched alkyl radical containing 6 carbon atoms designates the methyl, ethyl, propyl, isopropyl, butyl, isobutyl, sec-butyl, tert-butyl, pentyl, isopentyl, hexyl and isohexyl radicals as well as their linear or branched position isomers, the term linear or branched alkyl radical containing at most 4 carbon atoms designates the methyl, ethyl, propyl, isopropyl, butyl, isobutyl, sec-butyl and tert-butyl radicals as well as their linear or branched position isomers, the term linear or branched alkylene containing 6 carbon atoms designates the methylene, ethylene, propylene, isopropylene, butylene, isobutylene, sec-butylene, tert-butylene, pentylene, isopentylene, hexylene and isohexylene radicals as well as their linear or branched position isomers, the term linear or branched alkenylene radical containing 6 carbon atoms designates for example the vinylene, 1-propenylene, allylene, butenylene, 3-methyl-2-butenylene, 3-ethyl-2-butenylene radicals as well as their linear or branched position isomers, the term cycloalkyl radical designates the cyclopropyl, cyclobutyl radicals and quite particularly the cyclopentyl, cyclohexyl and adamentyl radicals, the term aryl radical designates the unsaturated, monocyclic radicals or constituted by condensed, carbocyclic rings. As examples of such an aryl radical, the phenyl or naphthyl radicals can be mentioned the term heteroaryl radical designates an aromatic ring comprising one or more nitrogen atoms: such a heteroaryl radical can be linked by a nitrogen atom or by a carbon atom: by way of non-exhaustive examples, there can be mentioned in particular the pyridyl, 2H-pyrrolyl, pyrrolyl, pyridinyl, furanyl, quinolinyl, isoquinolinyl, quinazolinyl, thienyl, benzothienyl radicals, and also the imidazolyl, pyrazolyl, pyrazinyl, pyrimidinyl, pyridazinyl, delta-2-imidazolinyl or also delta-3-pyrazolinyl radicals the term arylalkyl radical designates the radicals in which the aryl radical remainder and the alkyl radical remainder are chosen from the values indicated above in the respective definitions of aryl and alkyl: thus there can be mentioned for example the benzyl, phenethyl, phenylpropyl, phenylbutyl, phenylpentyl, phenylhexyl, naphthylmethyl, naphthylethyl, naphthylpropyl, naphthylbutyl or also naphthylpentyl radicals as well as their linear or branched position isomers, it being understood as indicated above that these radicals are optionally substituted on the aryl radical remainder and/or on the alkyl radical remainder the term halogen atom designates the chlorine, fluorine, bromine or iodine atom, and preferably the chlorine or bromine atom the term linear or branched alkenyl radical containing 4 carbon atoms designates in particular the vinyl, 1-propenyl, allyl, butenyl, 3-methyl-2-butenyl radicals as well as their linear or branched position isomers, the term linear or branched alkylthio radical containing at most 4 carbon atoms designates radicals such as in particular the methylthio, ethylthio, propylthio, isopropylthio, butylthio, isobutylthio, sec-butylthio, tert-butylthio radicals as well as their linear or branched position isomers the term linear or branched alkoxy radical designates the methoxy, ethoxy, propoxy, isopropoxy, linear, secondary or tertiary butoxy, pentoxy or hexoxy radicals as well as their linear or branched position isomers, the —NR4R5, NHR4, COR4, COOR4 and CONHR4 radicals designate in particular the N(alk)(alk), NH(alk), NH2, COalk, COalk, COOH, —C(O)—NH2 and —C(O)—NH(alk) radicals in which alk designates a linear or branched alkyl radical containing preferably at most 4 carbon atoms and also designates these same radicals in which the alkyl radical is replaced by a phenyl radical, these alkyl and phenyl radicals are optionally substituted as indicated above the term acid function or acid isostere designates the free, salified or esterified carboxy radical, the free or salified tetrazolyl radical, or the following radicals: —SO3H, —PO(OH)$_2$, —NH—SO2-CF3, —NH—SO2-NH—V, —NH—SO2-NH—CO—V, —NH—CO—V, —NH—CO—NH—V, —NH—CO—NH—SO2-V, —SO2-NH2, —SO2-NH—CO—V, —SO2-NH—CO—NH—V, —CO—NH—V, —CO—NH—OH, —CO—NH—SO2-V in which V represents a linear or branched alkyl or alkenyl radical, containing at most 6 carbon atoms or a phenyl radical, these alkyl, alkenyl and phenyl radicals which represent V being optionally substituted by the substituents indicated above for the alkyl and phenyl radicals of the products of formula (I).

The carboxy radical or radicals of the products of formula (I) can be salified or esterified by the various groups known to a person skilled in the art among which there can be mentioned, for example:

among the salification compounds, mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylethanolamine, tris(hydroxymethyl)amino methane, ethanolamine, pyridine, picoline, dicyclohexylamine, morpholine, benzylamine, procaine, lysine, arginine, histidine, N-methylglucamine, among the esterification compounds, the alkyl radicals in order to form the alkoxy carbonyl groups such as, for example, methoxycarbonyl, ethoxycarbonyl, tert-butoxycarbonyl or benzyloxycarbonyl, these alkyl radicals being able to be substituted by radicals chosen for example from the halogen atoms, the hydroxyl, alkoxy, acyl, acyloxy, alkylthio, amino or aryl radicals such as, for example, in the chloromethyl, hydroxypropyl, methoxymethyl, propionyloxymethyl, methylthiomethyl, dimethylaminoethyl, benzyl or phenethyl groups.

The addition salts with mineral or organic acids of the products of formula (I) can be, for example, the salts formed with hydrochloric, hydrobromic, hydroiodic, nitric, sulphuric, phosphoric, propionic, acetic, trifluoroacetic, formic, benzoic, maleic, fumaric, succinic, tartaric, citric, oxalic, glyoxylic, aspartic, ascorbic acids, the alkylmonosulphonic acids such as for example methanesulphonic acid, ethanesulphonic acid, propanesulphonic acid, the alkyldisulphonic acids such as for example methanedisulphonic acid, alpha, beta-ethanedisulphonic acid, the arylmonosulphonic acids such as benzenesulphonic acid and the aryldisulphonic acids.

It should be remembered that stereoisomerism can be defined in its broadest sense as the isomerism of compounds having the same structural formulae, but the different groups of which are arranged differently in space, such as in particular in monosubstituted cyclohexanes the substituent of which can be in the axial or equatorial position, and the different possible rotational configurations of ethane derivatives. However, another type of stereoisomerism exists, due to the different spatial arrangements of fixed substituents, either on the double bonds, or on the rings, which is often called geometric isomerism or cis-trans isomerism. The term stereoisomers is used in the present Application in its widest sense and therefore relates to all of the compounds indicated above.

Therefore a subject of the present invention is the products of formula (I) as defined above corresponding to the formula (Ia):

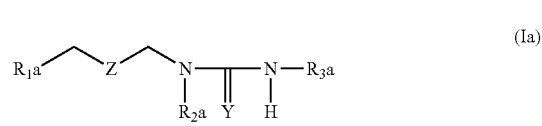

in which:

Y represents the oxygen or sulphur atom,

Z represents the divalent C=CH2, CH—CH3 or CH2 radical,

R1a represents a hydrogen atom, an optionally substituted morpholinyl radical or a diaminated radical of formula:

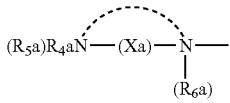

which represents either a saturated:

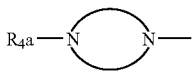

radical
or an unsaturated:

radical
or the:

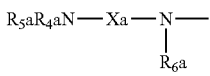

radical
in which the continuous arc indicates that the two nitrogen atoms form a heterocyclic radical chosen from the imidazolyl, pyrazolyl, pyrazinyl, pyrimidinyl, pyridazinyl, furazannyl, imidazolidinyl, delta-2-imidazolinyl, pyrazolidinyl, delta-3-pyrazolinyl, piperazinyl or also homopiperazinyl radicals, these heterocyclic radicals being optionally substituted by a free or esterified carboxy, phenyl, alkyl or phenylalkyl radical in which the alkyl radical is linear or branched containing at most 4 carbon atoms, Xa represents a carbonyl, linear or branched alkylene or alkenylene radical containing at most 6 carbon atoms optionally interrupted by an oxygen or sulphur atom, R4a, R5a and R6a, identical or different, are chosen from the hydrogen atom, the protective groups of the nitrogen atom, the linear or branched alkyl containing at most 4 carbon atoms, cycloalkyl containing at most 6 members, phenyl and phenylalkyl radicals, these alkyl, cycloalkyl, phenyl and phenylalkyl radicals being themselves optionally substituted, R2a represents a linear or branched alkyl radical containing at most 6 carbon atoms optionally substituted by one or more identical or different radicals chosen from the optionally substituted phenyl radical and the —NR4aR5a radical in which R4a and R5a, identical or different, have the meaning indicated above, R3a represents a linear or branched alkyl containing at most 6 carbon atoms, cycloalkyl containing 5 or 6 members, adamentyl, pyridinyl, quinolinyl, phenyl or phenylalkyl radical in which the alkyl radical is linear or branched containing at most 4 carbon atoms, all these radicals being optionally substituted, it being understood that all the cycloalkyl, alkyl, phenyl and phenylalkyl radicals indicated above as being optionally substituted, are optionally substituted by one or more identical or different radicals chosen from the halogen atoms, the hydroxyl, phenyl, phenoxy, trifluoromethyl, cyano, free, salified or esterified carboxy radicals, the linear or branched alkyl, alkenyl, alkylthio or alkoxy radicals containing at most 4 carbon atoms and the —NR4aR5a radical in which R4a and R5a, identical or different, have the meaning indicated above, all the phenyl and phenylalkyl radicals being moreover optionally substituted by a dioxol radical formed on two consecutive carbon atoms of the phenyl radical considered, said products of formula (Ia) being in all the possible racemic, enantiomeric and diastereoisomeric isomer forms, as well as the addition salts with mineral and organic acids or with mineral and organic bases of said products of formula (Ia).

A more particular subject of the present invention is the products of formula (I) as defined above corresponding to the formula (Ib):

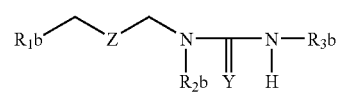

(Ib)

in which:

Y represents the oxygen or sulphur atom,

Z represents the divalent C═CH2 CH, —CH3 or CH2 radical,

R1b is as such or R1b represents a hydrogen atom or a piperazinyl or homopiperazinyl radical optionally substituted by a linear or branched alkyl radical containing at most 4 carbon atoms or a free or esterified carboxy radical, or $R_1b$ represents the

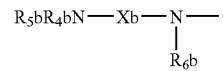

radical
in which Xb represents a carbonyl or alkylene radical, linear or branched, containing at most 6 carbon atoms, R4b, R5b and R6b, identical or different, are chosen from the hydrogen atom; the carboxy radical esterified by a linear or branched alkyl radical containing at most 4 carbon atoms; the linear or branched alkyl radicals containing at most 4 carbon atoms; the cycloalkyl containing at most 6 members; phenyl; benzyl and phenethyl radicals; all these alkyl, cycloalkyl, phenyl, benzyl and phenethyl radicals being themselves optionally substituted by one or more identical or different radicals chosen from the halogen atoms, the hydroxyl, phenyl, phenoxy, trifluoromethyl, cyano, free, salified or esterified carboxy radicals, the linear or branched alkyl, alkenyl, alkylthio or alkoxy radicals containing at most 4 carbon atoms and the —NH2 radical in which the hydrogen atoms are optionally substituted by one or two linear or branched alkyl radicals containing at most 4 carbon atoms, R2b represents a linear or branched alkyl radical containing at most 6 carbon atoms optionally substituted by one or more identical or different radicals chosen from the optionally substituted phenyl radical and the —NH2 radical in which one or two hydrogen atoms are optionally substituted by one or two identical or different substituents chosen from the linear or branched alkyl radical containing at most 4 carbon atoms and the phenyl radical itself optionally substituted, all these phenyl radicals being optionally substituted by one or more radicals chosen from the halogen atoms, the hydroxyl, phenyl, phenoxy, trifluoromethyl, free, salified or esterified carboxy radicals and the linear or branched alkyl and alkoxy radicals containing at most 4 carbon atoms, R3b represents a linear or branched alkyl containing at most 4 carbon atoms, cyclohexyl, cyclopentyl, adamentyl, phenyl or phenylalkyl radical in which the alkyl radical is linear or branched containing at most 4-carbon atoms and the phenyl radical is optionally substituted by one or more identical or different radicals chosen from the halogen atoms, the hydroxyl, phenyl, phenoxy, trifluoromethyl, cyano, free, salified or esterified carboxy radicals, the linear or branched alkyl, alkenyl, alkylthio and alkoxy radicals containing at most 4 carbon atoms and the —NH2 radical in which the hydrogen atoms are optionally substituted by one or two linear or branched alkyl radicals containing at most 4 carbon atoms, all the phenyl, benzyl and phenethyl radicals being moreover optionally substituted by a dioxol radical formed on two consecutive carbon atoms of the phenyl radical considered, said products of formula (Ib) being in all possible racemic, enantiomeric and diastereoisomeric isomer forms, as well as the addition salts with mineral and organic acids or with mineral and organic bases of said products of formula (Ib).

A more particular subject of the present invention is also the products of formula (I) as defined above corresponding to the formula (Ic):

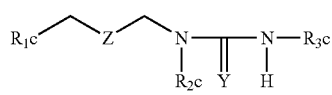

(Ic)

in which:

Y represents the oxygen atom,

Z represents the divalent C=CH2 or CH—CH3 radical,

R1c is chosen from the hydrogen atom and the piperazinyl and homopiperazinyl radicals linked by a nitrogen atom and optionally substituted on their second nitrogen atom by a linear or branched alkyl radical containing at most 4 carbon atoms or a free or esterified carboxy radical (—COOtBu)), or $R_1c$ represents the

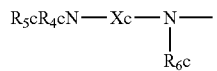

radical in which Xc represents a carbonyl or alkylene radical, linear or branched, containing at most 4 carbon atoms, R4c, R5c and R6c, identical or different, are chosen from the hydrogen atom; the carboxy radical esterified by a linear or branched alkyl radical containing at most 4 carbon atoms; the cyclohexyl radical optionally substituted by an NH2 radical in which the hydrogen atoms are optionally substituted by one or two linear or branched alkyl radicals containing at most 4 carbon atoms; the linear or branched alkyl radicals containing at most 4 carbon atoms; the phenyl radicals; benzyl and phenethyl radicals themselves optionally substituted by one or more identical or different radicals chosen from the halogen atoms, the hydroxyl, phenyl, phenoxy, trifluoromethyl, cyano, free, salified or esterified carboxy radicals, the linear or branched alkyl, alkenyl, alkylthio and alkoxy radicals containing at most 4 carbon atoms and the dioxol radical formed on two consecutive carbon atoms of the phenyl radical considered, R2c represents a linear or branched alkyl radical containing at most 6 carbon atoms optionally substituted by one or two radicals chosen from the phenyl and NH2 radicals, the phenyl radicals themselves being optionally substituted by a phenyl, linear or branched alkyl or alkoxy radical containing at most 4 carbon atoms and the —NH2 radical being optionally substituted on the one or two hydrogen atoms by one or two radicals chosen from linear or branched alkyl containing at most 4 carbon atoms and phenyl itself optionally substituted by a linear or branched alkyl radical containing at most 4 carbon atoms, R3c represents a linear or branched alkyl radical containing at most 4 carbon atoms, cyclohexyl, adamentyl, phenyl or phenylalkyl in which the alkyl radical contains at most 2 carbon atoms and the phenyl radical is optionally substituted by one or more identical or different radicals chosen from the halogen atoms, the hydroxyl, phenyl, phenoxy, trifluoromethyl, cyano, free, salified or esterified carboxy radical, the linear or branched alkyl, alkenyl, alkylthio or alkoxy radicals containing at most 4 carbon atoms and the dioxol radical formed on two consecutive carbon atoms of the phenyl radical considered, said products of formula (Ic) being in all possible racemic, enantiomeric and diastereoisomeric isomer forms, as well as the addition salts with mineral and organic acids or with mineral and organic bases of said products of formula (Ic).

A quite particular subject of the present invention is the products of formula (I) as defined above, corresponding to the formulae of the products of Examples 4 to 8, 23 to 82 and 97 to 106 described hereafter in the experimental part.

A subject of the present invention is also the process for the preparation of the products of formula (I), as defined above, characterized in that a compound of formula (II):

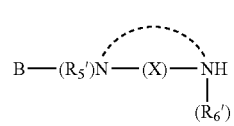

(II)

in which B represents either R4' which has the meaning indicated above for $R_4$ in which the optional reactive functions are optionally protected by protective groups or RL which represents a remainder of a resin linked via a linker, for example via a carbamate bond, X, R5' and R6' have the meanings indicated above respectively for X, R5 and R6, in which the optional reactive functions are optionally protected by protective groups, is subjected to a reaction with a compound of formula (III):

in which Hal represents a halogen atom and Z1 represents the divalent C=CH2 or CH2 radical, in order to obtain the product of formula (IV):

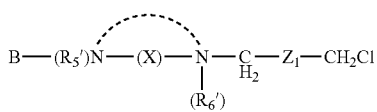
(IV)

in which B, X, Z1, R5' and R6' have the meanings indicated above, which product of formula (IV) is subjected to a reaction with a compound of formula (V)

 (V)

in which R2' has the meaning indicated above for R2, in which the optional reactive functions are optionally protected by protective groups, in order to obtain a product of formula (VI):

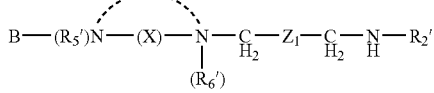
(VI)

in which B, X, Z1, R2', R5' and R6' have the meanings indicated above, which is subjected to a reaction with a compound of formula (VII):

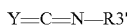 (VII)

in which R3' has the meaning indicated above for R3, in which the optional reactive functions are optionally protected by protective groups and Y represents the oxygen or sulphur atom, in order to obtain a product of formula (VIII):

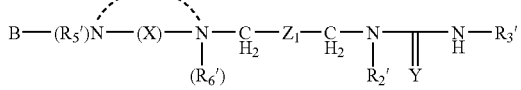
(VIII)

in which B, X, Y, Z1, R2', R3', R5' and R6' have the meanings indicated above, which product of formula (VIII) when B represents R4' constitutes a product of formula (Ix1):

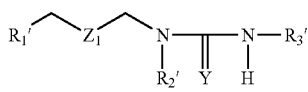
(Ix1)

in which R1' has the meaning indicated above for R1, in which the optional reactive functions are optionally protected by protective groups and R2', R3', Y and Z1 have the meanings indicated above, which product of formula (Ix1) when Z1 represents C=CH2, can be converted to the product of formula (Ix2):

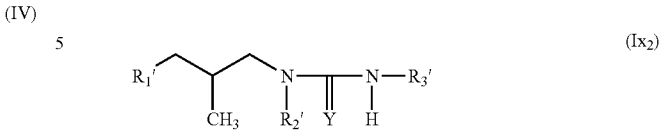
(Ix2)

in which R1', R2', R3' and Y, have the meanings indicated above, which product of formula (VIII) when B represents a remainder of resin RL as defined above, can be subjected to a cleavage reaction in order to obtain a product of formula (Iy1):

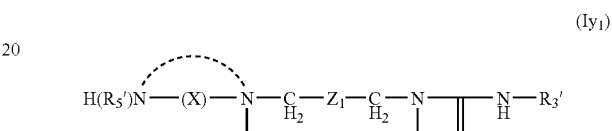
(Iy1)

in which X, Y, Z1, R2', R3', R5' and R6' have the meanings indicated above, which product of formula (Iy1) when Z1 represents C=CH2, can be converted to the product of formula (Iy2):

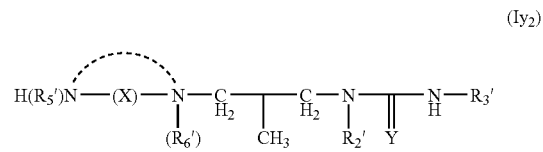
(Iy2)

in which X, Y, R2', R3', R5' and R6' have the meanings indicated above, which product of formula (V) as defined above can also be reacted with the aldehyde of formula (IX):

 (IX)

in order to obtain a product of formula (X):

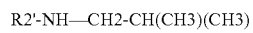 (X)

in which R2' has the meaning indicated above, which product of formula (X) is reacted with the product of formula (VII) as defined above in order to obtain the product of formula (Iz):

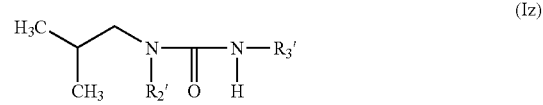
(Iz)

in which R2' and R3' have the meanings indicated above, which products of formulae (VIII) in the form of (Ix1) and (Iy1) and products of formulae (Ix2), (Iy2) and (Iz) can be the products of formula (I) and which, in order to obtain products or other products of formula (I), can be subjected, if desired and if necessary, to the one or more of the following conversion reactions, in any order:

a) an esterification reaction of the acid function,
b) a saponification reaction of the ester function to an acid function,
c) an oxidation reaction of the alkylthio group to a corresponding sulphoxide or sulphone,
d) a conversion reaction of the ketone function to an oxime function,
e) a reduction reaction of the free or esterified carboxy function to an alcohol function,
f) a conversion reaction of the alkoxy function to a hydroxyl function, or also of the hydroxyl function to an alkoxy function,
g) an oxidation reaction of the alcohol function to an aldehyde, acid or ketone function,
h) a conversion reaction of the nitrile radical to tetrazolyl or also a conversion reaction of the amine radical to a carbamate or urea or also a conversion reaction of an amine to sulphonamide or carboxamide,
i) an elimination reaction of the protective groups which can be carried by the protected reactive functions,
j) a salification reaction by a mineral or organic acid or by a base in order to obtain the corresponding salt,
k) a resolution reaction of the racemic forms to resolved products,
said products of formula (I) thus obtained being in all possible racemic, enantiomeric and diastereoisomeric isomer forms.

A subject of the present invention is also the process for the preparation of the products of formula (IIR) corresponding to formula (II) as defined in claim 6 when B represents RL:

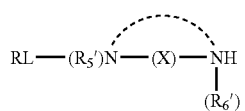
(IIR)

in which RL represents a resin remainder linked via a linker, X, R5' and R6' have the meanings indicated above for X, R5 and R6 respectively, in which the optional reactive functions are optionally protected by protective groups,
characterized in that a resin r containing an NH2 group:

r-NH2 is subjected to a reaction with a linker l having a carboxy function and a benzyl alcohol:

COOH-l-OH in order to obtain a product of formula (IX) having a free benzyl alcohol:

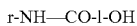
r-NH—CO-l-OH (IX)

in which r and l have the meanings indicated above,
which is reacted with 1-1 carbonylimidazole in order to obtain the product of formula (X):

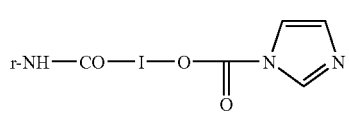
(X)

in which r and l have the meanings indicated above,
which is reacted with an amine of formula (XI):

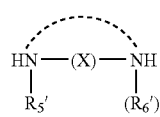
(XI)

in which R5', X and R6' have the meanings indicated above, in order to obtain the product of formula (IIR):

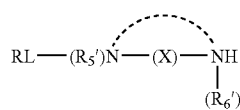
(IIR)

in which RL represents the

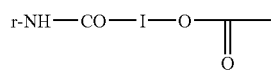

group
with r and l as defined above.

It should be noted that such conversion reactions of substituents to other substituents can also be carried but on the starting products as well as on the intermediates as defined above before continuing the synthesis according to the reactions indicated in the process described above.

Under preferred conditions for implementing the invention, the process described above can be carried out as follows. The process describe above shows that the products of formula (I) of the present Application can be synthesized under the same conditions according to two types of synthesis, one in solution and the other on solid phase, B representing R4 as defined above in the case of the synthesis in solution and B representing a resin associated to a linker in the case where the synthesis is carried out on solid phase. The solid phase is thus constituted by a resin attached to the starting molecule of formula (II) via a linker.

The reaction of the product of formula (II) with a product of formula (III) in order to produce a product of formula (IV) can be carried out in particular in the presence of DIEA (diisopropylethylamine) or also triethylamine (TEA) in a solvent such as THF or $CH_2Cl_2$ or also DMF.

The products of formula (IV) thus obtained are subjected to the action of the product of formula (V) as defined above in particular in DMF in order to produce a product of formula (VI) as defined above.

The products of formula (VI) are subjected to the action of the product of formula (VII) as defined above in particular in THF, DME, $CH_2Cl_2$ or also DMF in order to produce a product of formula (VIII) as defined above.

In the product of formula (VIII) thus obtained, B therefore represents R4 or a remainder of a resin.

when B represents R4, the products of formula (VIII) represent one part of the products of formula (I) which is called (Ix1).

The conversion reaction of the products of formula (Ix1) to products of formula (Ix2) can be carried out in particular by catalytic hydrogenation of the double bond for example with palladium on carbon.

When B represents a remainder of a resin, the products of formula (VIII) are subjected to a cleavage reaction releasing from the resin the corresponding products of formula (Iy1). Such a cleavage reaction is carried out in particular by trifluoroacetic acid in methylene chloride.

The conversion reaction of the products of formula (Iy1) to products of formula (Iy2) can be carried out in particular by catalytic hydrogenation of the double bond as indicated above for the conversion of the products of formula (Ix1) to products of formula (Ix2).

The reaction of the product of formula (V) with the product of formula (IX) as defined above in order to obtain a product of formula (X) can be carried out by a reducing amination reaction according to the usual methods known to a person skilled in the art in particular using NaBH3CN as reducing agent.

The products of formula (X) thus obtained are reacted with the products of formula (VII) as defined above in particular in a solvent such as in particular $CH_2Cl_2$ or DMF in order to generate the products of formula (Iz) which therefore constitute the products of formula (I) in which R1 represents a hydrogen atom and Z represents —CH—CH3.

According to the values of B, R1', R2', R3', R5' and R6', the products of formulae (VIII), (Ix1), (Iy1), (Ix2), (Iy2) and (Iz) can be or cannot be the products of formula (I): thus in order to obtain products of formula (I) or in order to convert them to other products of formula (I), the products of formulae (VIII), (Ix1), (Iy1), (Ix2), (Iy2) and (Iz) can be subjected to one or more of the reactions a) to k) indicated above.

Thus the various reactive functions which can be carried by certain compounds of the reactions defined above can, if necessary, be protected: it is for example the hydroxyl, acyl, free carboxy or also amino and monoalkylamino radicals which can be protected by the appropriate protective groups.

The following, non-exhaustive, list of examples of the protection of the reactive functions can be mentioned:

the hydroxyl groups can be protected for example by the alkyl radicals such as tert-butyl, trimethylsilyl, tert-butyldimethylsilyl, methoxymethyl, tetrahydropyrannyl, benzyl or acetyl, the amino groups can be protected for example by the acetyl, trityl, benzyl, tert-butoxycarbonyl, benzyloxycarbonyl, phthalimido radicals or other radicals known in peptide chemistry, the acyl groups such as the formyl group can be protected for example in the form of cyclic or non-cyclic ketals or thioketals such as dimethyl or diethylketal or ethylene dioxyketal, or diethylthioketal or ethylenedithioketal, the acid functions of the products described above can, if desired, be amidified by a primary or secondary amine, for example, in methylene chloride in the presence, for example, of 1-ethyl-3-(dimethylaminopropyl)carbodiimide hydrochloride at ambient temperature:

the acid functions can be protected for example in the form of esters formed with easily-cleavable esters such as benzyl or terbutyl esters or esters known in peptide chemistry.

The amine functions of the compounds defined above, can be if necessary protected, as indicated above, for example by a group such as Boc or CH2-phenyl then can be released under the usual conditions known to a person skilled in the art.

The saponification reaction can be carried out according to the usual methods known to a person skilled in the art, such as for example in a solvent such as methanol or ethanol, dioxane or dimethoxyethane, in the presence of soda or potash.

The reactions to which the products of formulae (Ix1), (Ix2), (Iy1), (Iy2) and (Iz) as defined above can be subjected, if desired or if necessary, can be carried out, for example, as indicated hereafter.

a) The products described above can, if desired, be subjected, on the optional carboxy functions, to esterification reactions which can be carried out according to the usual methods known to a person skilled in the art.

b) The optional conversions of the ester functions to an acid function of the products described above can be, if desired, carried out under the usual conditions known to a person skilled in the art in particular by acid or alkaline hydrolysis for example by soda or potash in an alcoholic medium such as, for example, in methanol or also by hydrochloric or sulphuric acid.

c) The optional alkylthio groups of the products described above can be, if desired, converted to the corresponding sulphoxide or sulphone functions under the usual conditions known to a person skilled in the art such as for example by peracids such as for example peracetic acid or metachloroperbenzoic acid or also by ozone, oxone, sodium periodate in a solvent such as for example methylene chloride or dioxane at ambient temperature.

Obtaining the sulphoxide function can be encouraged by an equimolar mixture of the product containing an alkylthio group and the reagent such as in particular a peracid.

Obtaining the sulphone function can be encouraged by a mixture of the product containing an alkylthio group with an excess of the reagent such as in particular a peracid.

d) The conversion reaction of a ketone function to oxime can be carried out under the usual conditions known to a person skilled in the art, such as in particular an action in the presence of an optionally O-substituted hydroxylamine in an alcohol such as for example ethanol, at ambient temperature or while heating.

e) The optional free or esterified carboxy functions of the products described above can be, if desired, reduced to the alcohol function by methods known to a person skilled in the art: the optional esterified carboxy functions can be, if desired, reduced to the alcohol function by methods known to a person skilled in the art and in particular by lithium and aluminium hydride in a solvent such as for example tetrahydrofuran or also dioxane or ethyl ether.

The optional free carboxy functions of the products described above can be, if desired, reduced to the alcohol function in particular by boron hydride.

f) The optional alkoxy functions such as in particular methoxy of the products described above can be, if desired, converted to the hydroxyl function under the usual conditions known to a person skilled in the art for example by boron tribromide in a solvent such as for example methylene chloride, by pyridine hydrobromide or hydrochloride or also by hydrobromic or hydrochloric acid in water or trifluoroacetic acid under reflux.

g) The optional alcohol functions of the products described above can be, if desired, converted to the aldehyde or acid function by oxidation under the usual conditions known to a person skilled in the art such as for example by the action of manganese oxide in order to obtain the aldehydes or Jones reagent for accessing acids.

h) The optional nitrile functions of the products described above can be, if desired, converted to tetrazolyl under the usual conditions known to a person skilled in the art.

It is understood that the reactions described above can be carried out as indicated or also, if appropriate, according to other usual methods known to a person skilled in the art.

The conversion of an amine function to carbamate can be carried out by reaction of a chloroformate in the presence of a base or of any other intermediate obtained by adding an alcohol to a carbonyl reagent such as for example carbonyl diimidazole, phosgene, diphosgene, triphosgene.

The conversion of an amine function to urea can be carried out by reaction of an isocyanate in $CH_2Cl_2$ or DMF.

The conversion of an amine function to sulphonamide can be carried out by reaction with a sulphonyl chloride in a solvent such as methylene chloride or dimethylformamide.

The conversion of an amine function to carboxamide can be carried out by reaction with a carboxylic acid in the presence of a coupling agent such as for example DCC (dicyclohexylcarbodiimide) or other coupling agents known to a person skilled in the art.

i) The elimination of the protective groups such as for example those indicated above can be carried out under the usual conditions known to a person skilled in the art in particular by an acid hydrolysis carried out with an acid such as hydrochloric, benzene sulphonic or paratoluene sulphonic, formic or trifluoroacetic acid or also by a catalytic hydrogenation.

The phthalimido group can be eliminated by hydrazine.

A list of the different protective groups which can be used will be found for example in the Patent BF 2 499 995.

j) the products described above can, if desired, be the subject of salification reactions for example by a mineral or organic acid or by a mineral or organic base according to the usual methods known to a person skilled in the art.

k) The optional optically active forms of the products described above can be prepared by resolution of the racemics according to the usual methods known to a person skilled in the art.

Illustrations of such reactions defined above are given in the preparation of the examples described hereafter.

The products of formula (I) as defined above as well as their addition salts with acids or bases have useful pharmacological properties.

The products of the present invention can thus act at the level of the receptor of inorganic ions and in particular calcium and thus modulate one or more activities of a receptor of inorganic ions such as in particular the calcium receptor.

Thus the products of the present application acting at the level of calcium receptors can in particular be used for the treatment or prevention of diseases or disorders linked to an abnormal physiological behaviour at the level of the receptors of inorganic ions and in particular at the level of calcium receptors such as the calcium membrane receptors capable of bonding the extracellular calcium (Ca sensing receptor CaSR).

The products of the present invention as defined above, are allosteric ligands of the calcium receptor. The products of the present invention can thus possess similar effects to those of true agonists or antagonists of the calcium receptors.

The products of the present invention can thus be more particularly endowed with properties for the regulation of extracellular Ca++, the serum levels of PTH and calcitonin.

The products of the present invention can more particularly possess agonist properties for the calcium receptors and will thus have a calcimimetic effect.

The products of the present invention, as agonists of calcium receptors, could thus, in particular increase the effects of extracellular calcium on a calcium receptor by such a calcimimetic effect.

The products of the present invention could thus in particular be used to participate in a reduction of the serum levels of the parathyroid hormone called PTH: these products could in this way be used in particular for the treatment of diseases such as hypercalcemia and hyperparathyroidism.

The products of the present invention can also present a calcilytic character: thus, certain products of formula (I) as defined above could have properties allowing them to reduce bone resorption which depends directly on the fluctuation in the circulating levels of PTH: these products could be useful in particular for the treatment of diseases such as osteoporosis or Paget's disease.

The products of formula (I) of the present invention can also have antimitotic and anti-neurodegenerative properties.

These properties justify their use in therapeutics and a particular subject of the invention is, as medicaments, the products of formula (I) as defined above, said products of formula (I) being in all possible racemic, enantiomeric and diastereoisomeric isomer forms, as well as the addition salts with pharmaceutically acceptable mineral and organic acids or mineral and organic bases of said products of formula (I).

The products of the present invention can thus be useful for the treatment of physiological diseases or disorders requiring for their treatment or their prevention the use of calcimimetic or calcilytic products, modulators of the calcium effect on the inorganic ion receptors in particular calcium receptors.

Thus certain calcilytic products of the present invention could be useful for the therapeutic or prophylactic treatment of diseases which are caused, at least in part, by an undesired increase in bone resorption.

Diseases the treatment or the prevention of which require the use of the products of formula (I) as defined above, are in particular hypercalcemia, malignant humoral hypercalcemia, osteoporosis of whatever origin, osteopenia for example cause by bone metastasis or induced by immobilization, dental disorders for example diseases of the periodontium, parodontitis, periarticular erosions in rhumatoid arthritis, osteoarthritis, Paget's disease, hypoparathyroidism, osteosarcoma or the reconstruction of fractures.

The products of the present invention can thus be used for the treatment or prevention of diseases or disorders such as in particular:

mineral or bone homeostasis such as osteosarcoma, diseases of the periodontium, fractures, osteoarthritis, rhumatoid arthritis, diseases of the central nervous system, epilepsy, dementia, depression, states of anxiety, neurodegenerative diseases such as Alzheimer's disease, auto-immune diseases, transplant rejects, 'oesophageal achalasia, proliferative diseases such as cancers, malignant tumors, inflammations, allergies, certain infections, pain, cardiovascular diseases, restenosis, hypertension, cardiomyopathies, Raynaud's disease.

The products of formula (I) as defined above can quite particularly be used in the treatment of diseases requiring control of the hormone PTH at the plasmatic level.

The products of formula (I) as defined above can thus quite particularly be used in the treatment of hypercalcemia or hyperparathyroidism.

Such products are quite particularly useful for the treatment or prevention of hyperparathyroidism Certain medicaments, which are a subject of the invention, could also be of use, as antimitotics, in the chemotherapy of cancers or in the treatment of bone diseases or as antineurodegeneratives, in the treatment of Alzheimer's disease or in the treatment neuronal apoptosis.

A more particular subject of the invention is, as medicaments, the products of formula (I) corresponding to the formula (Ic) as defined above.

A quite particular subject of the invention is, as medicaments, the products described as examples illustrating the present invention in the experimental part hereafter.

A more particular subject of the invention is, as medicaments, the products of formula (I) as defined above corresponding to the products of Examples 4 to 8, 23 to 82 and 97 to 106 described hereafter in the experimental part.

The products of formula (I) as well as their pharmaceutically acceptable salts can be administered to animals, preferably to mammals and in particular to human beings as therapeutic or prophylactic medicaments.

They can be administered as such or in a mixture with one or more other compounds of formula (I) or also in the form of a pharmaceutical composition which contains, as active ingredient, an effective dose of at least one product of formula (I) and/or its pharmaceutically acceptable salts as well as excipients and/or additives which are current and pharmaceutically inert.

These pharmaceutical compositions can be administered by buccal route, by enteral or parenteral route or by local route as a topical application on the skin and mucous membranes or by injection by intravenous or intramuscular route.

The medicaments can therefore be administered orally, for example in the form of pills, tablets, coated tablets, film-coated tablets, granules, gelatin capsules and soft capsules, solutions, syrups, emulsions, suspensions or aerosol mixtures.

The administration can however be carried out by rectal route, for example in the form of a suppository or by parenteral route, for example in the form of injectable solutions or infusions, microcapsules or implants, by percutaneous route, for example in the form of ointments, solutions, pigments or colouring agents, by transdermic route (patches) or by other routes such as in the form of an aerosol or nasal spray.

The medicaments according to the present invention can therefore be in the form of pharmaceutical compositions containing one or more of the products of formula (I) as defined above.

Such pharmaceutical compositions can therefore constitute the form in which the products of formula (I) as defined above are used in their therapeutic application.

The pharmaceutical compositions according to the invention are prepared according to the usual methods, pharmaceutically inert, organic or inorganic excipients, being added to the compounds of formula (I) and/or their pharmaceutically acceptable salts.

These compositions can therefore be solids or liquids and be presented in all the pharmaceutical forms commonly used in human medicine, such as for example, plain or sugar-coated tablets, pills, lozenges, gelatin capsules, drops, granules, injectable preparations, ointments, creams or gels; they are prepared according to the usual methods.

For the production of pills, tablets, coated tablets and hard gelatin capsules, it is possible of use for example, lactose, maize starch or its derivatives, talc, stearic acid or its salts, etc.

Suitable supports for soft gelatin capsules or suppositories are for example fats, waxes semi-solid or liquid polyols, natural or modified oils etc. Appropriate vehicles for the preparation of solutions, for example injectable solutions, emulsions or syrups are for example water, alcohols, glycerol, polyols, sucrose, inverted sugars, glucose, vegetable oils, etc. Appropriate supports for microcapsules or implants are for example the copolymeres of glyoxilic acid and lactic acid.

The pharmaceutical preparations normally contain from 0.5% to 90% by weight of the products of formula (I) and/or their physiologically acceptable salts.

The active ingredient can be incorporated with the excipients usually used in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

In addition to the active ingredients and the excipients, the pharmaceutical preparations can contain additives such as for example diluting agents, disintegration agents, binding agents, lubricants, wetting agents, stabilisers, emulsifiers, preservatives, sweetening agents, coloring, flavouring or aromatizing agents, thickeners, buffering agents, and solvents or solubilizing agents or agents to obtain a delayed release effect and also salts to modify the osmotic pressure, coating agents or antioxidants.

They can also contain two or more products of formula (I) and/or their pharmaceutically acceptable salts as defined above. Moreover, in addition to at least one or more products of formula (I) and/or their pharmaceutically acceptable salts, they can contain at least one or more other active ingredients which can be used as therapeutics or prophylactics.

Such pharmaceutical compositions contain, as active ingredient, an effective dose of at least one product of formula (I) and/or its pharmaceutically acceptable salts as well as one or more pharmaceutically acceptable excipients and optionally one or more usual additives.

The present invention therefore extends to the pharmaceutical compositions containing at least one of the medicaments as defined above as active ingredient.

When the products of formula (I) are used, the doses can vary within broad limits and must be fixed as a function of the person to be treated. This depends for example on the compound employed or the nature and severity of the disease to be treated and whether severe or chronic conditions are found or whether a prophylactic treatment is used.

The pharmaceutical compositions normally contain from 0.2 to 500 mg, and preferably from 1 to 200 mg of a compound of formula (I) and/or their pharmaceutically acceptable salts. In the case of an administration by oral route, the daily dose varies in general from 0.01 to 100 mg/kg and preferably from 0.1 to 50 mg/kg, in particular from 0.1 to 5 mg/kg. For example for an adult of 75 kg a dose varying from 0.3 to 0.5 mg/kg can be envisaged.

In the case of an administration by intravenous route, the daily dose varies approximately from 0.01 to 100 mg/kg and preferably from 0.05 to 10 mg/kg.

The daily dose can be divided, in particular in the case of the administration of large quantity of active ingredient, into several, for example 2, 3 or 4 parts. If appropriate, as a function of the individual's behaviour, it may be necessary to administer the different doses in an increasing or decreasing manner. Apart from the use of the products of formula (I) as defined above as medicaments, their use can also be envisaged as a vehicle or support for active compounds in order to transport these active compounds specifically to a site of action (Drug targeting, see Targeted Drug Delivery, R. C. Juliano, Handbook of Experimental Pharmacology, Vol 100, Ed. Born, G. V. R. et al, Springer Verlag). The active compounds which can be transported are in particular those used for the treatment or prevention of the diseases mentioned above.

The pharmaceutical compositions according to the present invention thus containing the products of formula (I) as defined in claims 1 to 5 and/or their pharmaceutically acceptable salts can thus in particular be used for the treatment or prevention of diseases requiring the administration of agonist or antagonist products of the receptors of inorganic ions such as in particular the calcium receptors.

Therefore a particular subject of the present invention is the use of the products of formula (I) as defined above and/or their pharmaceutically acceptable salts for the preparation of medicaments intended for the treatment or prevention of diseases or disorders linked to an abnormal physiological behaviour at the level of the receptors of inorganic ions and in particular at the level of calcium receptors.

The pharmaceutical compositions according to the present invention can thus be used as medicaments for the therapeutic applications indicated above.

A particular subject of the present invention is the use of the products of formula (I) as defined above and/or of their pharmaceutically acceptable salts for the preparation of medicaments intended for the treatment or the prevention of bone metabolism diseases, cardiovascular diseases, cancers neurodegenerative diseases, diseases of the immune system, infectious, inflammatory diseases, autoimmune diseases, hypercalcemia or hyperparathyroidism.

A more particular subject of the present invention is the products of formula (I) as defined above and/or of their pharmaceutically acceptable salts for the preparation of medicaments intended for the prevention or the treatment of bone metabolism diseases, cancers, neurodegenerative diseases, hypercalcemia or hyperparathyroidism A quite particular subject of the present invention is the use of the products of formula (I) as defined in claims 1 to and/or of their pharmaceutically acceptable salts for the preparation of medicaments intended for the prevention or the treatment hypercalcemia or hyperparathyroidism.

In particular a subject of the present invention is the use of the products of formula (I) as defined above and/or of their pharmaceutically acceptable salts for the preparation of medicaments intended for the prevention or the treatment of bone metabolism diseases and quite particularly the prevention or the treatment of osteoporosis.

In the process for the preparation of the products of formula (I) as defined above, the starting products of formulae (II), (III), (V), (VII) and (XI) as defined above can be known and obtained commercially or can be prepared according to the usual methods known to a person skilled in the art.

In particular certain starting products can also be prepared from commercial products for example by subjecting them to one or more of the reactions described above in a) to k), carried out under the conditions also described above.

Examples of compounds of formula (XI) called 1x are described in FIG. 1 below.

Examples of compounds of formula (V) called 2x are described in FIG. 2 below.

Examples of compounds of formula (VII) called 3x are described in FIG. 3 below.

Figure 2:
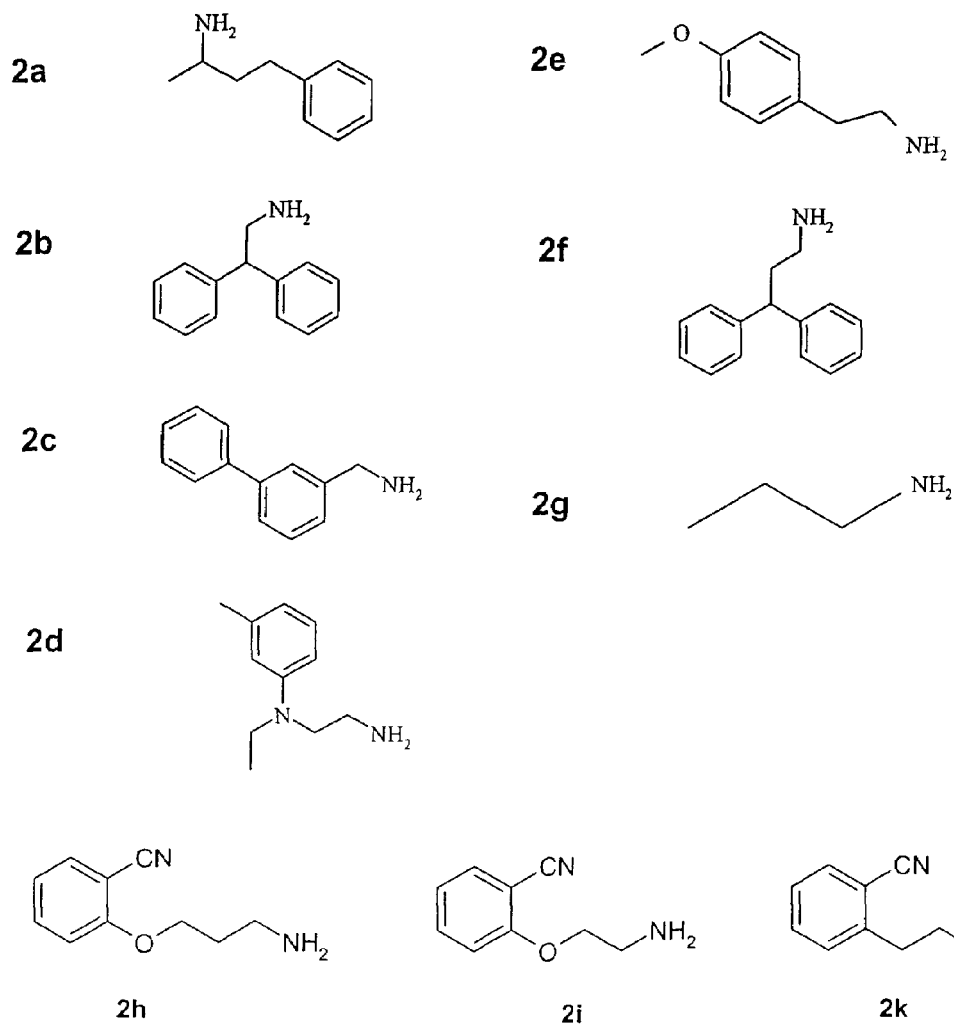
FIG. 2 describes 7 compounds of formula (V): 2a to 2g.
Figure 3A:
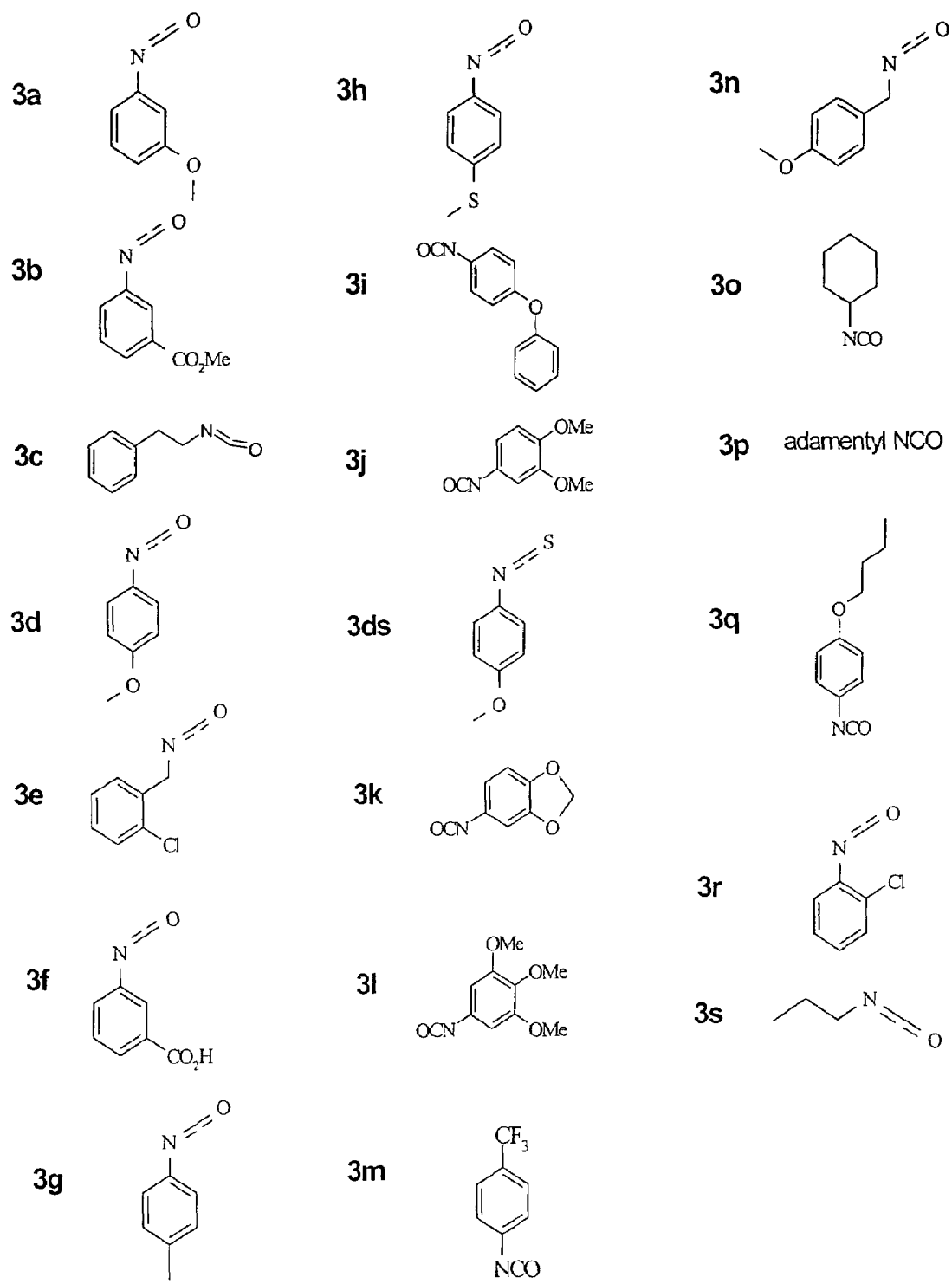
FIG. 3a describes 19 compounds of formula (VII): 3a to 3s.
Figure 3B:
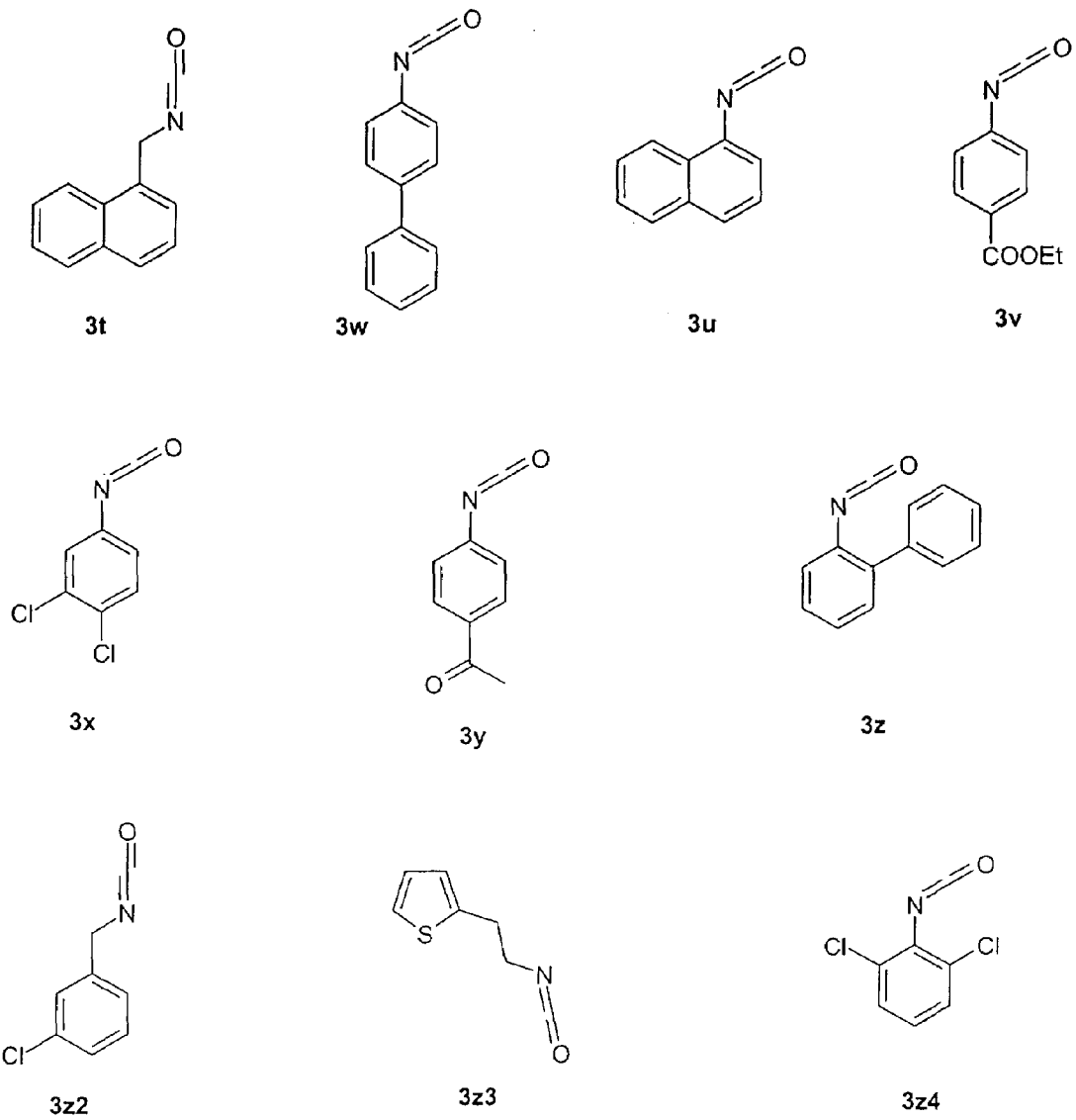
FIG. 3b describes 10 compounds: 3t to 3z, 3z2, 3z3, and 3z4.
Figure 5C:
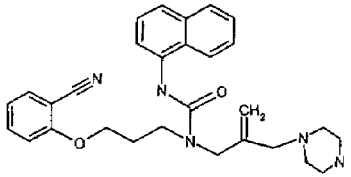
FIG. 5c represents a table of analytic MH+ results.
Figure 5C:
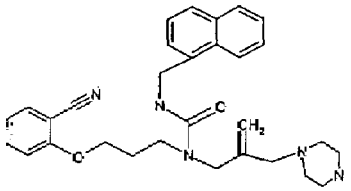
Figure 5C:
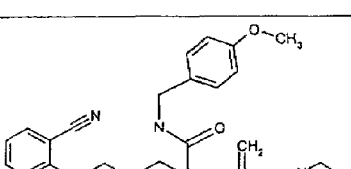
Figure 5C:
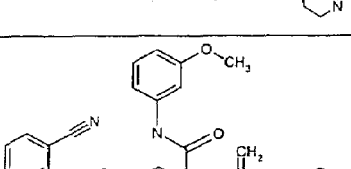
Figure 5C:
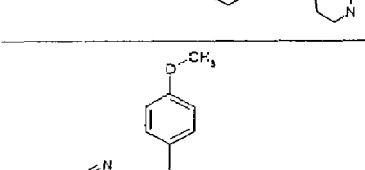
Figure 5C:
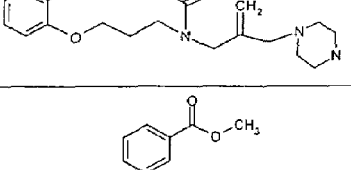
Figure 5C:
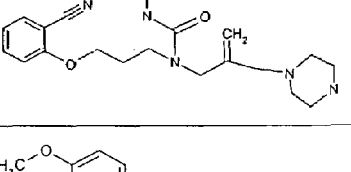
Figure 5D:
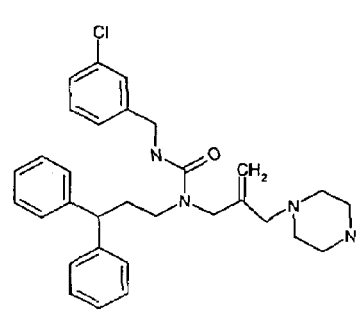
FIG. 5d represents a table of analytic MH+ results.
Figure 5D:
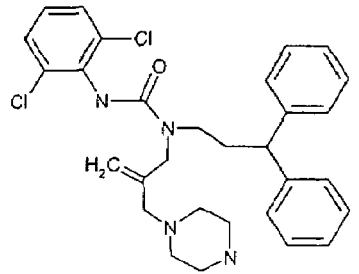
Figure 5D:
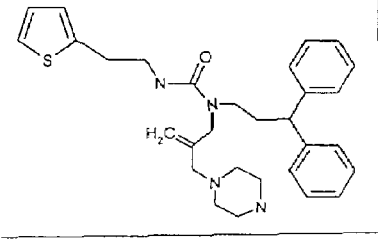
Figure 5D:
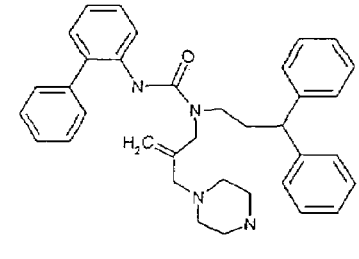
Figure 5D:
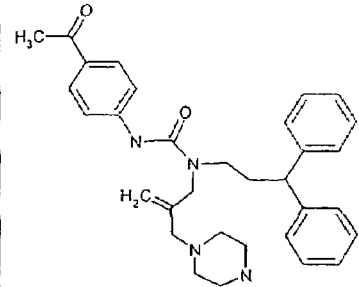

In compounds 1x, 2x and 3x indicated above, the variable x represents the letters of the alphabet a, b, c, etc, each number and associated letter corresponding to a precise compound described in FIGS. 1, 2 and 3 described hereafter.

FIG. 1 describes 14 compounds of formula (XI): 1a to 1n.
FIG. 2 describes 7 compounds of formula (V): 2a to 2g.
FIG. 3 describes 19 compounds of formula (VII): 3a to 3s.

The starting products of formula (II) in which B represents RL are used for the process on solid phase and can be prepared as indicated above.

The resin r-NH2 can be in particular a polystyrene resin with an NH2 residue or also a TentaGel resin with an NH2 residue or also any other type of resin known to a person skilled in the art allowing the direct attachment or via a linker of amine R1 as defined above.

The linker 1 can be for example HMPB or 4-hydroxymethyl-3-methoxyphenoxybutyric acid or other linkers known to a person skilled in the art.

The starting products of formula (II) in which B represents R4' as defined above are commercial products or can be prepared according to the usual methods known to a person skilled in the art.

As products of formula (II) in which B represents R4' as defined above, there can be mentioned in particular N-boc piperazine and N-boc-homopiperazine.

The starting product of formula (IX) or isobutyraldehyde is known and commercially available.

In the starting product of formula (III), Hal represents a halogen atom chosen from chlorine, bromine or iodine.

Among the commercial starting products of formulae (III), (V), (VII) and (XI), there can be mentioned for example:
  as products of formula (III): 3-chloro-2-chloromethyl-1 propene, 3-chloro-2-chloromethyl-1 propane, 1,3 dichloropropane, 1,3 dibromopropane or also 1,3 diiodopropane.
  as products of formula (XI): piperazine, homopiperazine, 1,2 diaminocyclohexane, N,N-dimethyl-1,3 ethanediamine, N,N-dimethyl-1,3 propanediamine.
  as products of formula (V): 3,3 diphenylpropylamine, 3,3 diphenylethylpropylamine or 3 phenylpropylamine.
  as products of formula (VII): 2 chloro-benzylisocyanate, 3-methoxyphenylisocyanate, 4-methoxyphenylisocyanate or 3-carbomethoxyphenylisocyanate.

The experimental part hereafter gives examples of such starting products.

The following examples illustrate the invention without however limiting it.

The products in the examples of the present Application have been prepared either, for Examples 1 to 23 and 74 to 130, according to the synthesis process on solid phase from the starting product of formula (II) in which B represents RL as defined above or, for Examples 24 to 73, according to the synthesis process in solution from the starting product of formula (II) in which B represents R4' as defined above.

In the preparations described hereafter:

The solvents and reagents used are commercial products which are used directly except where indicated otherwise. The anhydrous solvents are dried on 4 Å molecular sieves.

The thin layer chromatographies (TLC) were carried out on ready-to-use glass-backed analytical plates covered with KIESELGEL® 60F$_{254}$ or RP-18F$_{254}$ (MERCK) silica gel. The compounds are visualized:
  by extinction of the fluorescence during exposure under UV light at 254 nm.
  or by iodine vapour.

The chromatographies on a silica column have been carried out with KIESELGEL® 60 silica gel (granulometry 0.063-0.200 mm; MERCK). The elution solvents are specified in each operating method.

The NMR spectra were recorded in solution in deuterochloroform (CDCl$_3$) except where specified otherwise, with tetramethylsilane (TMS) as internal reference, a BRUKER AC-300 device with a superconductor magnet of 7.05T (the proton $^1$H resonates at 300 MHz and carbon $^{13}$C at 75 MHz). The chemical shifts (δ) are expressed in ppm positively with respect to the TMS, the solvent being taken as external reference. For the protons spectrum, they are followed by the following abbreviations: s, bs, d, dd, t, q, quint and m used to designate singlet, broad singlet, doublet, doublet of doublet, triplet, quadruplet, quintuplet and multiplet respectively.

The NMR results are given hereafter with the preparation of the products described in the examples.

The mass spectr MH+ were recorded on an Autospec (Micromass) Platform II (Micromass) device operating in electrospray mode: FIG. 4 hereafter gives a table of such analytic MH+ results for the products of Examples 1 to 22, 74 to 82 and 99 to 130, the preparation of which is described hereafter

I) EXAMPLES 1 TO 23 AND 74 TO 130

Synthesis on Solid Phase

The general synthesis process on solid phase is described hereafter.

Stage 1: TG-NH—HMPB—OH 80 mg (0.1475 mmol) of Aminomethyl polystyrene resin (origin Polymer Laboratories bead size 150-300 μm) 1.84 mmol/g is introduced which is swollen in 2.7 ml of DMF then the resin is washed with 3 times 2 ml of DMF. Another 1 ml of DMF is added then 1.23 ml of a 0.45M solution prepared from:

HMPB 4-(4-hydroxymethyl-3-methoxy phenoxy)-butyric acid 0.84 g
HOBT 1-hydroxy benzotriazole hydrate 0.52 g
DMF dimethylformamide 8 ml is added.

Stirring is carried out for 10 minutes then 123 μl of DIC (diisopropylcarbodiimide) is introduced into each reactor.

Stirring is carried out for three hours at ambient temperature followed by washing successively with 5 times 2 ml of DMF and 5 times 2 ml of THF (tetrahydrofuran).

Stage 2: TG-NH—HMPB—O—CO—R1': Product of Formula (II) (Introduction of R1 with the Product of Formula (XI), cf FIG. 1)

1 ml of THF (tetrahydrofuran) then 1.25 ml of a 0.4 M solution of 1,1-carbonyldiimidazole in anhydrous THF are introduced into each reactor.

Stirring is carried out for 1 hour at ambient temperature then another 1.25 ml of a 0.4M solution of 1,1-carbonyldiimidazole in THF is introduced.

Stirring is carried out for 1 hour at ambient temperature then the resin is washed 5 times with 3 ml of anhydrous THF. 2.5 ml of a 1.5 M solution of diamine of the product 1× of formula (XI) as defined in FIG. 1 hereafter is introduced into N-methylpyrrolidinone. Stirring is carried out for 12 hours at 50° C. then the resin is washed with 3 times 2 ml of methylene chloride, with 3 times 2 ml of methanol then with 6 times 2 ml of dimethylsulphoxide.

Stage 3: Product of Formula (IV)

1 ml of DMSO (dimethylsulphoxide) then 1.48 ml of a 1M solution of 3-chloro 2-chloromethylpropene in DMSO are introduced into each reactor. After 10 minutes under nitrogen bubbling, 263 μl of N,N Diisopropylethylamine is introduced into each reactor. Stirring is carried out for 24 hours at ambient temperature then the resins are washed with 3 times 3 ml of DMF (dimethylformamide) then with 4 times 3 ml of DMSO (dimethylsulphoxide).

Stage 4: Product of Formula (VI) (Introduction of R2 with the Product of Formula (V) cf FIG. 2)

1 ml of DMSO (dimethylsulphoxide) then 1.48 mmol of a 1.4 M solution of primary amine 2× of formula (V) as defined in FIG. 2 hereafter in DMSO are introduced. Stirring is carried out for forty hours at ambient temperature then the resin is washed 6 times with 3 ml of DMF (dimethylformamide).

Stage 5: Product of Formula (VIII) (Introduction of R3 with the Product of Formula (VII) cf FIG. 3)

1 ml of DMF (dimethyl-formamide) then 1.3 mmol of a 1M solution of isocyanate 3× of formula (VII) as defined in FIG. 3 hereafter in DMF (dimethylformamide) are introduced into each reactor. The reaction medium is left under stirring for 12 hours at ambient temperature then washed 4 times with 3 times 3 ml of DMF (dimethylformamide) then 1 ml of methanol.

Stage 6: Product of Formula (Ix1)

2 ml of methylene chloride then 0.5 ml of TFA (trifluoroacetic acid) are introduced into each reactor. Stirring is carried out for 1 hour at ambient temperature then the chloromethylene solution is filtered then taken to dryness.

The products are purified on a silica cartridge in an eluent mixture of CH2Cl2 90/methanol 10.

Examples 1 to 23 and 74 to 130 which follow have been prepared according to the conditions described above for synthesis on solid phase using for each of these examples:

in Stage 2, adequate compound 1x of formula (XI) for the introduction of the substituent R1,
in Stage 4, adequate compound 2x of formula (V) for the introduction of the substituent R2,
in Stage 5, adequate compound 3x of formula (VII) for the introduction of the substituent R3, the compounds 1x, 2x and 3x indicated above being respectively described in FIGS. 1, 2 and 3 described hereafter.

The other Stages 1, 3, 6 and if appropriate Stage 7 of the synthesis of Examples 1 to 23 and 74 to 130 which follow are as defined above in the general synthesis process.

In order to describe the preparation of Examples 1 to 23 and 74 to 130, there are indicated hereafter for each of these examples the compounds of formulae 1x, 2x and 3x as defined above indicated in FIGS. 1, 2 and 3 hereafter, respectively used as indicated in the general process above.

Example 1

N-(3-methoxyphenyl)-N'-(4-phenyl-2-butyl)-N'-[2-[(piperazin-1-yl)methyl]-2-propen-1-yl]-urea Compounds 1a, 2a and 3a.

Example 2 methyl 3-[[[(4-phenyl-2-butyl)[2-[(piperazin-1-yl)methyl]-2-propen-1-yl]amino]carbonyl]amino]-benzoate Compounds 1a, 2a and 3b.

Example 3

N'-(4-phenyl-2-butyl)-N-(2-phenylethyl)-N'-[2-[(piperazin-1-yl)methyl-2-propen-1-yl]-urea Compounds 1a, 2a and 3c.

Example 4

N'-(2,2-diphenylethyl)-N-(2-phenylethyl)-N'-[2-[(piperazin-1-yl)methyl]-2-propen-1-yl]-urea Compounds 1a, 2b and 3c.

Example 5

N'-(2,2-diphenylethyl)-N-(4-methoxyphenyl)-N'-[2-[(piperazin-1-yl)methyl]-2-propen-1-yl]-urea Compounds 1a, 2b and 3d

Example 6

N'-(2,2-diphenylethyl)-N'-[2-[(piperazin-1-yl)methyl]-2-propen-1-yl]-N[2-(chlorophenyl)methyl]-urea Compounds 1a, 2b and 3e.

Example 7 methyl 3-[[[(2,2-diphenylethyl)[2-[(piperazin-1-yl)methyl]-2-propen-1-yl]-amino]carbonyl]amino]-benzoate Compounds 1a, 2b and 3b.

Example 8

N'-(2,2-diphenylethyl)-N-(3-methoxyphenyl)-N'-[2-[(piperazin-1-yl)methyl]-2-propen-1-yl]-urea Compounds 1a, 2b and 3a.

Example 9 methyl 3-[[[[(1,1'-biphenyl-3-yl)methyl][2-[(piperazin-1-yl)methyl]-2-propen-1-yl-amino]carbonyl]amino]benzoate Compounds 1a, 2c and 3b.

Example 10

N'-[(1,1'-biphenyl-3-yl)methyl]-N-(3-methoxy-phenyl)-N'-[2-[(piperazin-1-yl)methyl]-2-propen-1-yl]-urea Compounds 1a, 2c and 3a.

Example 11

N-[(2-chlorophenyl)methyl]-N'-[(1,1-biphenyl-3-yl)methyl]-N'-[2-[(piperazin-1-yl)methyl]-2-propen-1-yl]-urea Compounds 1a, 2c and 3e.

Example 12

N'-[(1,1'-biphenyl-3-yl)methyl]-N-(2-phenylethyl)-N'-[2-[(piperazin-1-yl)methyl]-2-propen-1-yl]-urea Compounds 1a, 2c and 3c.

Example 13

N-(3-methoxyphenyl)-N'-[[(3-methylphenyl)-ethylamino]ethyl]-N'-[2 [(piperazin-1-yl)methyl]-2-propen-1-yl]-urea Compounds 1a, 2d and 3a.

Analytical results: NMR (1H, DMSO) 1.09 (t) 3H CH3-CH2-N 3.34 (q) 2H CH3-CH2-N 2.21 (s) 3H CH3-phenyl 2.53 (m); 3.05 (m) 8H the N—CH2's of the ring 2.97 (bs) 2H, 4.01 (bs) 2H N—CH2-C(=CH2)-CH2-N 5.06 (bs); 5.12 (bs) 2H N—CH2-C(=CH2)—CH2-N 3.72 (s) 3H CH3-O-phenyl 3.42 (bs) 4H N—CH2-CH2-N 6.43 (bd) Hb or Hd 6.53 (dd) Hh 6.58 (bs) Ha 6.56(d) Hd or Hb 7.04 (m) Hc 7.14(t) Hg 7.10 (dd) Hc 6.98 (ddd) Hf 8.50 (bs) 2H NH2+8.02 (bs) 1H NH—C=O

Example 14 methyl 3-[[[[2-[(3-methylphenyl)ethylamino]ethyl][2-[(piperazin-1-yl)methyl]-2-propen-1-yl]amino]carbonyl]amino]-benzoate Compounds 1a, 2d and 3b.

Analytical results: NMR (1H, DMSO) 1.07 (t) 3H CH3-CH2-N 3.35 (bq) 2H CH3-CH2-N 2.20 (s) 3H CH3-phenyl 2.56 (masked); 3.04 (bs) 8H the N—CH2's of the ring 3.04 (bs) 2H, 4.03 (bs) 2H N—CH2-C(=CH2)-CH2-N 5.06 (bs); 5.15 (bs) 2H N—CH2-C(=CH2)—CH2-N 3.85 (s) 3H CH3-O—C=O 3.42 (b) 4H N—CH2-CH2-N 6.42 (d) 1H Hd 6.57 (bs) 2H Ha or Hb 7.04 (bt) Hc 7.40 (t) Hg 7.56 (bd) Hf 8.10 (dd) He 7.75 (bd) Hh 8.53 (bs) 1H NH-C=O 8.58 (bs) 2H NH2+

Example 15

N-[(2-chlorophenyl)methyl]-N'-[2-[(3-methylphenyl)ethylamino]ethyl]-N'-[2-[(piperazin-1-yl)methyl]-2-propen-1-yl]-urea Compounds 1a, 2d and 3e.

Example 16

N'-[2-[(3-methylphenyl)ethylamino]ethyl]-N'-[2-[(piperazin-1-yl)methyl]-2-propen-1-yl]-N-(2-phenylethyl)-urea Compounds 1a, 2d and 3c.

Example 17

N'-[2-[(3-methylphenyl)ethylamino]ethyl]-N-(4-methoxyphenyl)-N'-[2-[(piperazin-1-yl)methyl]-2-propen-1-yl]-urea Compounds 1a, 2d and 3d.

Example 18

N'-[2-(4-methoxyphenyl)ethyl]-N-(3-methoxyphenyl)-N'-[2-[(piperazin-1-yl)methyl]-2-propen-1-yl]-urea Compounds 1a, 2e and 3a.

Example 19 methyl 3-[[[[2-(4-methoxyphenyl)ethyl][2-[(piperazin-1-yl)methyl]-2-propen-1-yl-amino]carbonyl]amino]-benzoate Compounds 1a, 2e and 3b.

Example 20

N'-[2-(4-methoxyphenyl)ethyl]-N-(2-phenylethyl)-N'-[2-[(piperazin-1-yl)methyl]-2-propen-1-yl]-urea Compounds 1a, 2e and 3c.

Example 21

N-[(2-chlorophenyl)methyl]-N'-[2-(4-methoxyphenyl)ethyl]-N'-[2-[(piperazin-1-yl)methyl]-2-propen-1-yl]-urea Compounds 1a, 2e and 3e.

Example 22

N-(4-methoxyphenyl)-N'-[2-(4-methoxyphenyl)ethyl]-N'-[2-[(piperazin-1-yl)methyl]-2-propen-1-yl]-urea Compounds 1a, 2e and 3d.

Example 23

N'-(3,3-diphenyl-1-propyl)-N-(2-phenylethyl)-N'-[2-[(piperazin-1-yl)methyl]-2-propen-1-yl]-urea Compounds 1b, 2f and 3a.

Example 74 methyl 3-[[[propyl[2-[(piperazin-1-yl)methyl]-2-propen-1-yl]amino]carbonyl]amino]-benzoate Compounds 1a, 2g and 3b.

Example 75

N-propyl-N-[2-[(piperazin-1-yl)methyl]-2-propenyl]-N'-[(2-chlorophenyl)methyl]-urea Compounds 1a, 29 and 3r.

Analytical results: NMR (1H, DMSO) 0.84 (t) 3H C$\underline{H}$3-CH2-CH2-N 1.52 (m) 2H CH3-C$\underline{H2}$-CH2-N 3.15 (m) 2H CH3-CH2-C$\underline{H2}$-N 2.97 (bs) 2H, 3.87 (bs) 2H N—C$\underline{H2}$-C(=CH2)-C$\underline{H2}$-N 5.00 (bs); 5.08 (bs) 2H N—CH2-C(=C$\underline{H2}$)-CH2-N 2.56 (m); 3.07 (m) 8H the N—C$\underline{H2}$'s of the ring 4.33 (bd) 2H phenyl-C$\underline{H2}$—NH 6.65 (bt) 1H phenyl-CH2-N$\underline{H}$ 8.48 (bs) 1H mobile H 7.20 to 7.41 (m) 5H phenyl

Example 76

N'-(3,3-diphenyl-1-propyl)-N'-[2-[(hexahydro-1H-1,4-diazepin-1-yl)methyl]-2-propen-1-yl]-N-(3-methoxyphenyl)-urea Compounds 1e, 2f and 3a.

Example 77 methyl 3-[[[(3,3-diphenyl-1-propyl)[2-[(hexahydro-1H-1,4-diazepin-1-yl)methyl]-2-propen-1-yl]-amino]carbonyl]-amino]-benzoate Compounds 1e, 2f and 3b.

Example 78

N'-(3,3-diphenyl-1-propyl)-N'-[2-[(hexahydro-1H-1,4-diazepin-1-yl)methyl]-2-propen-1-yl]-N-(4-methylphenyl)-urea Compounds 1e, 2f and 39.

Example 79

N'-(3,3-diphenyl-1-propyl)-N'-[2-[(hexahydro-1H-1,4-diazepin-1-yl)methyl]-2-propenyl]-N-(4-methoxyphenyl)-urea hydrochloride Compounds 1e, 2f and 3d.

Example 80

N'-(3,3-diphenyl-1-propyl)-N'-[2-[(hexahydro-1H-1,4-diazepin-1-yl)methyl]-2-propen-1-yl]-N-[(2-chlorophenyl)-methyl]-urea Compounds 1e, 2f and 3r.

Example 81

N'-(3,3-diphenyl-1-propyl)-N'-[2-[(hexahydro-1H-1,4-diazepin-1-yl)methyl]-2-propen-1-yl]-N-(2-phenylethyl)-urea Compounds 1e, 2f and 3c.

Example 82

N'-(3,3-diphenyl-1-propyl)-N'-[2-[(hexahydro-1H-1,4-diazepin-1-yl)methyl]-2-propen-1-yl]-N-propyl-urea Compounds 1e, 2f and 3s.

Example 83 cis)-N''-(2-aminocyclohexyl)-N-(3,3-diphenyl-1-propyl)-N,N''-(2-methylene-1,3-propanediyl)bis[N'-(3-methoxyphenyl)]-urea Compounds 1f, 2f and 3a.

Example 84

(cis)methyl 3,3'-[7-(2-aminocyclohexyl)-2,8-dioxo-3-(3,3-diphenylpropyl)-5-methylene-1,3,7,9-tetraaza-1,9-nonane-diyl]bis benzoate Compounds 1g, 2f and 3b.

Example 85

(cis) N''-(2-aminocyclohexyl)-N-(3,3-diphenyl-1-propyl)-N,N'''-(2-methylene-1,3-propanediyl)bis-[N'-(4-methyl-phenyl)]-urea Compounds 1h, 2f and 3g.

Example 86

(cis)-N''-(2-aminocyclohexyl)-N-(3,3-diphenyl-1-propyl)-N,N'''-(2-methylene-1,3-propanediyl)bis-[N'-(4-methoxyphenyl)]-urea Compounds 1i, 2f and 3d.

Example 87

(cis)-N''-(2-aminocyclohexyl)-N-(3,3-diphenyl-1-propyl)-N,N'''-(2-methylene-1,3-propanediyl)bis-[N'-(2-chlorophenyl)]-urea Compounds 1j, 2f and 3e.

Example 88

(cis)-N''-(2-aminocyclohexyl)-N-(3,3-diphenyl-1-propyl)-N,N'''-(2-methylene-1,3-propanediyl)bis-[N'-(2-phenylethyl)]-urea Compounds 1k, 2f and 3c.

Example 89

(cis)-N''-(2-aminocyclohexyl)-N-(3,3-diphenyl-1-propyl)-N,N'''-(2-methylene-1,3-propanediyl)bis-[N'-propyl]-urea Compounds 1l, 2f and 3s.

Example 90

(trans)-N''-(2-aminocyclohexyl)-N-(3,3-diphenyl-1-propyl)-N,N'''-(2-methylene-1,3-propanediyl)bis-[N'-(3-methoxyphenyl)]-urea Compounds 1f, 2f and 3a.

Example 91

(trans) methyl 3,3'-[7-(2-aminocyclohexyl)-2,8-dioxo-3-(3,3-diphenylpropyl)-5-methylene-1,3,7,9-tetraaza-1,9-nona-nediyl]bis benzoate Compounds 1g, 2f and 3b.

Example 92

(trans)-N''-(2-aminocyclohexyl)-N-(3,3-diphenyl-1-propyl)-N,N'''-(2-methylene-1,3-propanediyl)bis-[N'-(4-methylphenyl)]-urea Compounds 1h, 2f and 3g.

Example 93

(trans)-N''-(2-aminocyclohexyl)-N-(3,3-diphenyl-1-propyl)-N,N'''-(2-methylene-1,3-propanediyl)bis-[N'-(4-methoxyphenyl)]urea Compounds 1i, 2f and 3d.

Example 94

(trans)-N''-(2-aminocyclohexyl)-N-(3,3-diphenyl-1-propyl)-N,N'''-(2-methylene-1,3-propanediyl)bis-[N'-(2-chlorophenyl)]-urea Compounds 1j, 2f and 3e.

Example 95

(trans)-N''-(2-aminocyclohexyl)-N-(3,3-diphenyl-1-propyl)-N,N'''-(2-methylene-1,3-propanediyl)bis-[N'-(2-phenylethyl)]-urea Compounds 1k, 2f and 3c.

Example 96

(trans)-N''-(2-aminocyclohexyl)-N-(3,3-diphenyl-1-propyl)-N,N'''-(2-methylene-1,3-propanediyl)bis-[N'-propyl]-urea Compounds 1l, 2f and 3s.

Example 97

N-(3,3-diphenylpropyl)-N-[2-[[[3-(methylamino)-propyl]methylamino]methyl]-1-propen-2-yl]-N'-[(2-chlorophenyl)methyl]-urea Compounds 1m, 2f and 3e.

Example 98

N-(3,3-diphenylpropyl)-N-[2-[[[3-(methylamino)-propyl]methylamino]methyl]-1-propen-2-yl]-N'-(2-phenylethyl)-urea Compounds 1m, 2f and 3c.

Example 99

N-(3,3-diphenylpropyl)-N-[2-[[[3-(methylamino)-propyl]methylamino]methyl]-1-propen-2-yl]-N'-propyl urea Compounds 1m, 2f and 3s.

Example 100

N-(3,3-diphenylpropyl)-N-[2-[[[2-(methylamino)-ethyl]methylamino]methyl]-1-propen-2-yl]-N'-(3-methoxyphenyl)-urea Compounds 1n, 2f and 3a.

Example 101 methyl 3-[[[(3,3-diphenylpropyl)-[2-[[[2-(methylamino)ethyl]methylamino]methyl]-1-propen-2-yl]amino]carbonyl]amino]-benzoate Compounds 1n, 2f and 3b.

Example 102

N-(3,3-diphenylpropyl)-N-[2-[[[2 (methylamino)ethyl]methylamino]methyl]-1-propen-2-yl]-N'-(4-methylphenyl)-urea Compounds 1n, 2f and 39.

Example 103

N-(3,3-diphenylpropyl)-N-[2-[[[2-(methylamino)ethyl]methylamino]methyl]-1-propen-2-yl]-N'-(4-methoxyphenyl)-urea Compounds 1n, 2f and 3d.

Example 104

N'-[(2-chlorophenyl)methyl]-N-(3,3-diphenylpropyl)-N-[2-[[[2 (methylamino)ethyl]methylamino]methyl]-1-propen-2-yl]-urea Compounds 1n, 2f and 3e.

Example 105

N-(3,3-diphenylpropyl)-N-[2-[[[2-(methylaino)ethyl]methylamino]methyl]-1-propen-2-yl]-N'-(2-phenylethyl)-urea Compounds 1n, 2f and 3c.

Example 106

N-(3,3-diphenylpropyl)-N-[2-[[[2-(methylamino)ethyl]methylamino]methyl]-1-propen-2-yl]-N'-propyl-urea Compounds 1n, 2f and 3s.

Example 107 methyl 3-[[[(3,3-diphenylpropyl)[2-[[methyl[3-(methylamino)propyl]amino]methyl]-2-propenyl]-amino]-carbonyl]-amino]-benzoate Compounds 1m, 2f and 3b.

Example 108

N-(3,3-diphenylpropyl)-N-[2-[[methyl[3-(methylamino)propyl]amino]methyl]-2-propenyl]-N'-(4-methylphenyl)-urea Compounds 1m, 2f and 3g.

Example 109

N-(3,3-diphenylpropyl)-N-[2-[[methyl[3-(methylamino)propyl]amino]methyl]-2-propenyl]-N'-(4-methoxyphenyl)-urea Compounds 1m, 2f and 3d.

Example 110

N'-(3,4-dichlorophenyl)-N-(3,3-diphenylpropyl)-N-[2-(1-piperazinylmethyl)-2-propenyl-urea Compounds 1a, 2f and 3x.

Example 111

N-[2-(2-cyanophenoxy)ethyl]-N'-(3-methoxy-phenyl)-N-[2-(1-piperazinylmethyl)-2-propenyl]-urea Compounds 1a, 2l and 3a.

Example 112

N-[2-(2-cyanophenoxy)ethyl]-N'-(4-methoxyphenyl)-N-[2-(1-piperazinylmethyl)-2-propenyl]-urea Compounds 1a, 2l and 3d.

Example 113 methyl 3-[[[[2-(2-cyanophenoxy)ethyl][2-(1-piperazinylmethyl)-2-propenyl]amino]carbonyl]amino]-benzoate Compounds 1a, 2l and 3b.

Example 114

N-[2-(2-cyanophenoxy)ethyl]-N'-[(2-chlorophenyl)methyl]-N-[2-(1-piperazinylmethyl)-2-propenyl]-urea Compounds 1a, 2l and 3e.

Example 115

N-[2-(2-cyanophenoxy)ethyl]-N'-(1-naphthalenyl)-N-[2-(1-piperazinylmethyl)-2-propenyl]-urea Compounds 1a, 2l and 3u.

Example 116

N-[2-(2-cyanophenoxy)ethyl]-N'-(1,1' biphenyl)-4-yl-N-[2-(1-piperazinylmethyl)-2-propenyl]-urea Compounds 1a, 2h and 3w.

Example 117 methyl 4-[[[[3-(2-cyanophenoxy)propyl][2-(1-piperazinylmethyl)-2-propenyl]amino]carbonyl]amino]-benzoate Compounds 1a, 2h and 3v.

Example 118

N-[3-(2-cyanophenoxy)propyl]-N'-[(2-chlorophenyl)methyl]-N-[2-(1-piperazinylmethyl)-2-propenyl]-urea Compounds 1a, 2h and 3e.

Example 119

N-[3-(2-cyanophenoxy)propyl]-N'-(1-naphthalenyl)-N-[2-(1-piperazinylmethyl)-2-propenyl]-urea Compounds 1a, 2h and 3u.

Example 120

N-[3-(2-cyanophenoxy)propyl]-N''-[(1-naphthalenyl)methyl]-N-[2-(1-piperazinylmethyl)-2-propenyl]-urea Compounds 1a, 2h and 3t.

Example 121

N-[3-(2-cyanophenoxy)propyl]-N'-[(4-methoxyphenyl)methyl]-N-[2-(1-piperazinylmethyl)-2-propenyl]-urea Compounds 1a, 2h and 3n.

Example 122

N-[3-(2-cyanophenoxy)propyl]-N'-(3-methoxyphenyl)-N-[2-(1-piperazinylmethyl)-2-propenyl]-urea Compounds 1a, 2h and 3a.

Example 123

N-[3-(2-cyanophenoxy)propyl]-N'-(4-methoxyphenyl)-N-[2-(1-piperazinylmethyl)-2-propenyl]-urea Compounds 1a, 2h and 3d.

Example 124 methyl 3-[[[[3-(2-cyanophenoxy)propyl][2-(1-piperazinylmethyl)-2-propenyl]amino]carbonyl]amino]-benzoate Compounds 1a, 2h and 3b.

Example 125

N-(3,3-diphenylpropyl)-N'-[(4-methoxyphenyl)-methyl]-N-[2-(1-piperazinylmethyl)-2-propenyl]-urea Compounds 1a, 2f and 3n.

Example 126

N-(3,3-diphenylpropyl)-N'-[(3-chlorophenyl)-methyl]-N-[2-(1-piperazinylmethyl)-2-propenyl]-urea Compounds 1a, 2f and 3z2

Example 127

N'-(2,6-dichlorophenyl)-N-(3,3-diphenylpropyl)-N-[2-(1-piperazinylmethyl)-2-propenyl]-urea Compounds 1a, 2f and 3z4.

Example 128

N'-[2-(2-thienyl)ethyl]-N-(3,3-diphenylpropyl)-N-[2-(1-piperazinylmethyl)-2-propenyl]-urea Compounds 1a, 2f and 3z3.

Example 129

N'-(1,1'-biphenyl)-2-yl-N-(3,3-diphenylpropyl)-N-[2-(1-piperazinylmethyl)-2-propenyl-urea Compounds 1a, 2f and 3z1.

Example 130

N'-(4-acetylphenyl)-N-(3,3-diphenylpropyl)-N-[2-(1-piperazinylmethyl)-2-propenyl-urea Compounds 1a, 2f and 3y.

II) EXAMPLES 24 TO 73

Synthesis in Solution

Example 24

(1,1-dimethylethyl) 4-[2-[[(3,3-diphenyl-1-propyl)[[[3-(methoxycarbonyl)phenyl]amino]carbonyl]amino]methyl]-2-propen-1-yl]-piperazinecarboxylate Stage 1: (1,1-dimethylethyl) 4-(2-chlorophenylmethyl-2-propen-1-yl)-piperazinecarboxylate (6)

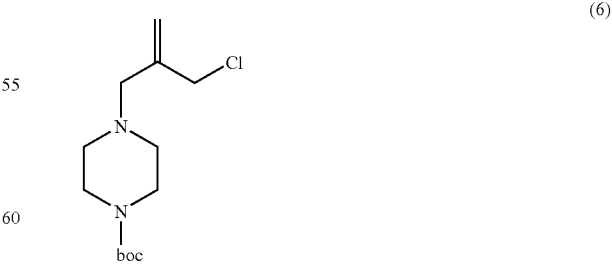

(6)

N-boc-piperazine (5 g, 26.8 mmol, 1 eq) is introduced in solution in 350 mL of acetonitrile into a 1 litre flask provided with a condenser. K$_2$CO$_3$ (3.8 g, 27.1 mmol, 1 eq), LiI (350 mg, 2.6 mmol, 0.1 eq) and finally 2-chloromethyl-3-chloropropene (16.8 g, 134.4 mmol, 5 eq) are then introduced successively. The system is then placed under reflux of the solvent for 1.5 hours.

The reaction medium is then taken up in water, and the organic phase is extracted with dichloromethane. The latter is dried over MgSO₄, filtered and the solvent is driven off under vacuum using a rotary evaporator.

The yellow oil obtained is then chromatographed on a silica column (eluent: 95/5 CH₂Cl₂/MeOH) for finally the expected product (6) is obtained also in the form of a yellow oil (4.82 g, η=65%).

Analytical results: T.L.C.: Rf: 0.69 (eluent: 95/5 CH₂Cl₂/MeOH, developer I₂) NMR: (200 MHz, CDCL3): δ (ppm) 1.38 (s, 9H, Ha), 2.28 (t, 2*2H, Hb), 2.96 (s, 2H, Hc), 3.35 (t, 2*2H, Hd), 4.04 (s, 1H, He), 5.07 and 5.20 (s, 1H, Hf and hf')

Stage 2: (1,1-dimethylethyl) 4-(2-(((3,3-diphenyl)propyl)amino)methyl-2-propen-1-yl)-piperazinecarboxylate (7)

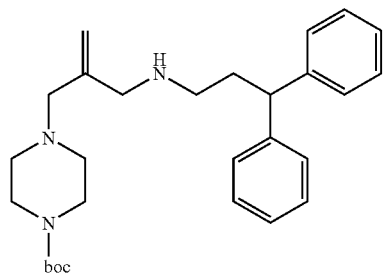

(7)

N-boc-chloroallylpiperazine (6) obtained in Stage 1 above (2.132 g, 7.76 mmol, 1 eq) in solution in 20 mL of acetonitrile is introduced into a 20 mL flask provided with a condenser. K₂CO₃ (1.09 g, 7.79 mmol, 1 eq) and 3,3-diphenylpropylamine (8.2 g, 38.8 mmol, 5 eq) are then introduced successively. The system is then placed under reflux of the solvent for 3 hours.

The reaction medium is taken in water, and the organic phase is extracted with dichloromethane. The latter is dried over MgSO₄, filtered and the solvent is driven off under vacuum using a rotary evaporator.

The yellow oil obtained is then chromatographed on a silica column (eluent: 93/7 then 9/1 CH₂Cl₂/MeOH) in order to finally obtained the expected product (7) also in the form of a yellow oil (2.90 g, η=83%).

Analytical results: TLC: Rf: 0.36 (eluent: 9/1 CH₂Cl₂/MeOH, developer I₂) NMR: (200 MHz, CDCL3): δ (ppm) 1.35 (s, 9H, Ha), 2.18 (m, 2*2H+2H, Hb and Hc), 2.45 (t, 2H, Hd), 2.79 (s, 2H, He), 3.10 (s, 2H, Hf), 3.26 (t, 2*2H, Hg and hg'), 3.90 (t, 1H, Hh), 4.88 and 4.90 (s, 1H, Hi and hi'), 7.00-7.20 (m, 10H, aromatic H).

Stage 3: (1,1-dimethylethyl) 4-[2-[[(3,3-diphenyl-1-propyl)[[[3-methoxycarbonyl)phenyl]amino]carbonyl]amino]methyl]-2-propen-1-yl]-piperazinecarboxylate The secondary amine (1 eq, 1 mmol) obtained in Stage 2 above is introduced into a flask in solution in dichloromethane (10 mL) then the isocyanate of formula 3b of Table 3 i.e. 3-carboxyphenylisocyanate is added.

The reaction medium is stirred for 2 hours at ambient temperature before being taken up in water. The organic phase is then extracted with dichloromethane, and the latter, after having been dried over MgSO₄, is then filtered and the solvent is driven off under vacuum using a rotary evaporator. After filtration of the crude reaction product on silica, the expected product is obtained in this way with a yield of 90%.

Analytical results: TLC: Rf: 0.73 (eluent: 9/1 CH₂Cl₂/MeOH) NMR: (DXP 300 MHz, CDCL3): δ (ppm) 1.45 (s, 9H, Ha), 2.36 (bs, 2*2H, Hb), 2.39 (m, 2H, Hc)/2.97 (s, 2H, Hd), 3.22 (dd, 2H, He), 3.42 (bs, 2*2H, Hf), 3.83 (s, 2H, Hg), 3.92 (t, 1H, Hh), 4.92 and 5.09 (s, 2*1H, Hi and Hi'), 3.88 (s, 3H, Hj), 7.18 and 7.27 (m, 2H+8H, aromatic H's), 7.36 (t, 1H, Hk), 7.69 and 7.80 (bd, 2*1H, Hl and Hm), 7.87 (bs, 1H, Hn), 8.91 (bs, 1H, Hn). MS: (electrospray in positive and negative modes): m/z=627.3 [MH]⁺; m/z=571.2 [MH-tBu]⁺; m/z=527.3 [MH-boc]⁺; m/z=625.3 [M−H]⁻

Example 25 methyl 3-[[[(3,3-diphenyl-1-propyl)[2-[(piperazin-1-yl)methyl]-2-propen-1-yl]amino]carbonyl]amino]-benzoate The operation for the deprotection of N-Boc to NH of the product of Example 24 is carried out

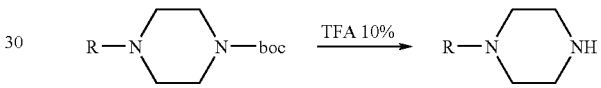

The product of Example 24 carrying an N-boc piperazine (1 eq, 3 mmol) is introduced in solution in dichloromethane (100 mL) into a flask. Trifluoroacetic acid ("normal grade" 10 mL) is then introduced dropwise. Once the introduction is finished, the reaction medium is stirred for 2 hours at ambient temperature. The solvent is then driven off under vacuum with a rotary evaporator and the residue is taken up in aqueous soda (2N), then the organic phase is extracted with dichloromethane. The latter, after having been dried over MgSO₄, is then filtered and the solvent driven off under vacuum using a rotary evaporator. Chromatography on a silica column is then carried out if necessary. In this way the expected product is obtained with a yield of approximately 85%.

Analytical results: TLC: Rf: 0.09 (eluent: 9/1 CH₂Cl₂/MeOH) NMR: (DXP 300 MHz, CDCL3): δ (ppm) 2.39 (m, 2H, Ha), 2.40 (m, 2*2H, Hb), 2.90 (m, 2*2H, Hc), 2.94 (s, 2H, Hd), 3.19 (m, 2H, He), 3.81 (s, 2H, Hf), 3.90 (s, 3H, Hg), 3.93 (masked, 1H, Hh), 4.89 and 5.07 (s, 2*1H, Hi and Hi'), 7.13-7.31 (m, 10H, aromatic H's), 7.36 (t, 1H, Hi), 7.70 (bd, 1H, Hm), 7.82 (bd, 1H, Hk), 7.96 (dd, 1H, Hj), 8.81 (bs, 1H, Hn). MS: m/z=527 [MH]⁺

Example 26 methyl 3-[[[(3,3-diphenyl-1-propyl)[2-[(piperazin-1-yl)methyl]-2-propen-1-yl]amino]carbonyl]amino]-benzoate hydrochloride 100 g of the product of Example 25 is solubilized in 2 ml of methanol then a few drops of a 6N solution of hydrochloric acid in methanol is added. The mixture is evaporated, taken up in 3 ml of water and filtered. The filtrate is lyophilized and in this way the expected hydrochloride is obtained with a yield of 92%.

Example 27

3-[[[(3,3-diphenyl-1-propyl)[2-[(piperazin-1-yl)methyl]-2-propenyl]amino]-carbonyl]amino]-Benzoic acid hydrochloride The operation starts from the product of Example 24 by treating with 5 equivalents of aqueous soda (2N) in methanol for 3 hours under reflux. After acidification with aqueous HCl to pH=2, extraction is carried out with $CH_2Cl_2$, followed by taking up in TFA as indicated in Example 25. In this way the expected product is obtained with a yield of 72%.

Example 28 methyl 3-[[[(3,3-diphenyl-1-propyl)[2-[(4-methylpiperazin-1-yl)methyl]-2-propen-1-yl]amino]-carbonyl]amino]-benzoate hydrochloride The operation is carried out according to the Eischweiler-Clark reaction for the methylation of NH to NCH3 of the product of Example 25 as follows.

The product of Example 25 (0.2 mmol, 1 eq) in 0.5 mL of MeOH is introduced into a 1 mL flask provided with a condenser. A 37% aqueous solution of formol (0.39 mmol, 1.95 eq) and formic acid (0.75 mmol, 3.75 eq) are then introduced successively. The reaction medium is then placed under reflux of methanol for 2 hours 30 minutes.

The reaction medium is then taken up in a solution of $NaHCO_3$ (1N), and the organic phase is extracted with dichloromethane. The latter is dried over $MgSO_4$, filtered and the solvent is driven off under vacuum using a rotary evaporator.

The residue obtained is chromatographed on a silica column (eluent: 95/5 $CH_2Cl_2$/MeOH) in order to finally obtain the expected product N-Me ((23) or (24)) with a yield of the order of 85%.

Analytical results: TLC: Rf: 0.40 (eluent: 9/1 $CH_2Cl_2$/MeOH) NMR: (DPX 300 MHz, CDCL3): δ (ppm) 2.33 (s, 3H, Ha), 2.39 (m, 2H, Hb), 2.48 (bs, 8H, Hc), 2.95 (s, 2H, Hd), 3.19 (m, 2H, He), 3.81 (s, 2H, Hf), 3.93 (t, 1H, Hg), 3.90 (s, 3H, Hh), 4.89 and 5.08 (bs, 2*1H, Hi and i'), 7.13-7.31 (m, 10H, aromatic H's), 7.37 (t, 1H, Hj), 7.70 (bd, 1H, Hk), 7.91 (m, 2H, Hl and Hm), 8.80 (bs, 1H, Hn). MS: (electrospray in positive and negative modes): m/z=541.3 $[MH]^+$; m/z=539.3 $[M-H]^-$

Example 29 methyl 3-[[[(3,3-diphenyl-1-propyl)[2-[(4-methylpiperazin-1-yl)methyl]-2-propen-1-yl]amino]-carbonyl]amino]-benzoate hydrochloride The operation is carried out as in Example 26 starting With the product of Example 28 instead of the product of Example 25 and in this way the expected product is obtained.

Example 30 methyl 3-[[[(3,3-diphenyl-1-propyl)[3-(piperazin-1-yl)-2-methyl-propyl]amino]carbonyl]amino]-benzoate hydrochloride The operation starts from 90 mg of the product of Example 24 by carrying out a catalytic hydrogenation overnight with 10 mg of palladium on carbon in 6 ml of methanol. After filtration and evaporation, the crude reaction product is purified on silica with $CH_2Cl_2$/MeOH: 90/10 as eluent. The purified product is obtained with a yield of 31%. The salt of the purified product thus obtained is prepared by proceeding as in Example 26 starting from 11 mg of the purified product thus obtained instead of the product of Example 25 and 9.7 mg of expected product is obtained with a yield of 82%.

In this way the expected product is obtained with an overall yield of 25%.

Example 31

(1,1-dimethylethyl) 4-[2-[[(3,3-diphenyl-1-propyl)[[(4-methyl-phenyl)amino]carbonyl]amino]methyl]-2-propen-1-yl]1-piperazinecarboxylate The operation is carried out as in Example 24 using the isocyanate 3g described in FIG. 3 hereafter in Stage 3 instead of the isocyanate 3b and in this way the expected product is obtained.

Analytical results: TLC: Rf: 0.38 (eluent: 93/7 $CH_2Cl_2$/MeOH) NMR: (DPX 300 MHz, $CDCL_3$): δ (ppm) 1.45 (s, 9H, Ha), 2.23 (s, 3H, Hb), 2.32 (m, 2*2H, Hc), 2.38 (m, 2H, Hd), 2.93 (s, 2H, He), 3.19 (m, 2H, Hf), 3.36 (bs, 2*2H, Hg), 3.80 (s, 2H, Hh) 3.92 (t, 1H, Hi), 4.91 and 5.05 (bs, 2*1H, Hj and Hj'), 7.08 and 7.23 (AA'BB', 4H, Hk, k' and Hl, l'), 7.11-7.32 (m, 10H, aromatic H's). MS: (electrospray in positive and negative modes): m/z=583.3 $[MH]^+$; m/z=527.2 $[MH-tBu]^+$; m/z=483.3 $[MH-boc]^+$; m/z=581.3 [M-H]

Example 32

N'-(3,3-diphenyl-1-propyl)-N-(4-methylphenyl)-N'-[2-[(piperazin-1-yl)methyl-2-propenyl]-urea The operation is carried out as in Example 25 in TFA/CH2Cl2 starting from the product of Example 31 instead of starting from the product of Example 24 in order to release the Nboc function to NH.

In this way the expected product is obtained.

Analytical results: TLC: Rf: 0.10 (eluent: 9/1 $CH_2Cl_2$/MeOH) NMR: (DPX 300 MHz, DMSO): δ (ppm) 2.20 (masked, 2*2H, Ha), 2.22 (s, 3H, Hb), 2.27 (m, 2H, Hc), 2.65 (bt, 2*2H, Hd), 2.80 (s, 2H, He), 3.10 (bt, 2H, Hf), 3.87 (bs, 2H, Hg), 4.82 and 4.97 (bs, 2*1H, Hh and Hh'), 7.02 (d, 2*1H, Hi and Hi'), 7.20-7.40 (m, 10H, aromatic H's), 7.29 (masked, 2*1H, Hj and Hj'), 8.34 (s, 1H, Hk). MS: m/z=483.3 $[MH]^+$; m/z=481.4 $[M-H]^-$

Example 33

N'-(3,3-diphenyl-1-propyl)-N-(4-methylphenyl)-N'-[2-[(4-methylpiperazin-1-yl)methyl]-2-propen-1-yl]-urea The operation is carried out as in Example 28 starting from the compound of Example 32 instead of the compound of Example 25 and the expected product is obtained with a yield of 49%.

Analytical results TLC: Rf: 0.36 (eluent: 9/1 $CH_2Cl_2$/MeOH) NMR: (DPX 300 MHz, CDCL3): δ (ppm) 2.28 (s, 3H, Ha), 2.30 (s, 3H, Hb), 2.32-2.50 (bs, 8H, Hc), 2.38 (m, 2H, Hd), 2.94 (bs, 2H, He), 3.18 (m, 2H, Hf), 3.79 (bs, 2H, Hg), 3.92 (t, 1H, Hh), 4.88 and 5.05 (bs, 2*1H, Hi and i'), 7.08 and 7.28 (AA'BB', 4H, Hi, i', j, j'), 7.12-7.35 (m, 10H, aromatic H's), 8.38 (bs, 1H, Hl). MS: (electrospray in positive and negative modes): m/z=497.3 $[MH]^+$; m/z=541.4 $(M-H]^-$+HCOOH

Example 34

N'-(3,3-diphenyl-1-propyl)-N'-[2-[(4-methylpiperazin-1-yl)methyl]-2-propen-1-yl]-N-(4-methylphenyl)-urea hydrochloride The operation is carried out as in Example 26 starting from the product of Example 33 instead of the product of Example 25 and in this way the expected salt is obtained with a yield of 92%.

Example 35

N'-(3,3-diphenyl-1-propyl)-N'-[3-(piperazin-1-yl)-2-methyl-propyl]-N-(4-methylphenyl)-urea The operation is carried out as in Example 30 starting from the product of Example 31 instead of the product of Example 24 and in this way the expected salt is obtained with a yield of 23%.

Example 36

N'-(3,3-diphenyl-1-propyl)-N-(4-methylphenyl)-N'-[2-[(piperazin-1-yl)methyl]-2-propen-1-yl]-urea hydrochloride The operation is carried out as in Example 26 starting from the product of Example 35 instead of the product of Example 25 and in this way the expected product is obtained with a yield of 94%.

Example 37

(1,1-dimethylethyl) 4-[2-[[[[[(2-chlorophenyl)methyl]amino]carbonyl] (3,3-diphenyl-1-propyl)amino]methyl]-2-propen-1-yl]-piperazinecarboxylate The condensation of isocyanates on the secondary amine (7) is carried out

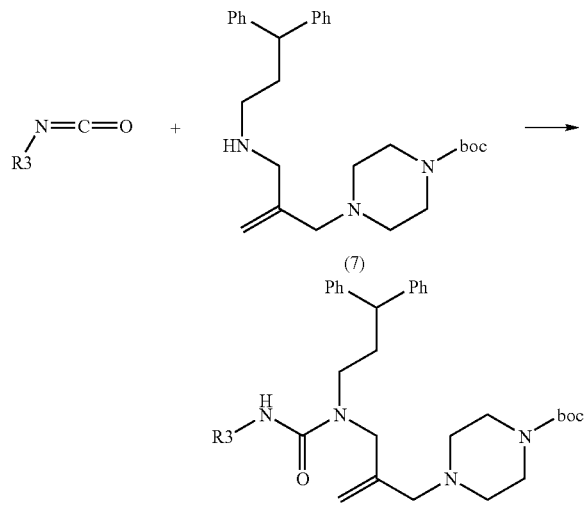

The secondary amine (7) obtained in Stage 2 of Example 24 (145 mg, 1 eq, 0.32 mmol) is introduced in solution in dichloromethane (10 mL) into tubes (10). Then the corresponding isocyanate (from 1.09 to 1.17 eq) is added to each tube. The reaction media are stirred for 2 hours at ambient temperature. The PS-Tisamine (reagent supported on resin) (3 eq/excess of isocyanate) is then introduced into each of the tubes, and the reaction media are stirred again for 45 minutes at ambient temperature. This operation is carried out again if any isocyanate remains. The resin is then eliminated by filtration, and the solvent is driven off using a centrifuge under vacuum (speedvac), in order to finally recover the desired product originating from the condensation carried out. In this way the desired urea is obtained with a yield of approximately 90%.

Analytical results: TLC: Rf: 0.14 (eluent: 9/1 $CH_2Cl_2$/AcOEt) NMR: (DPX 300 MHz, $CDCl_3$): δ (ppm) 1.44 (s, 9H, Ha), 2.22 (m, 2*2H, Hb), 2.33 (m, 2H, Hc), 2.86 (bs, 2H, Hd), 3.16 (masked, 2H, He), 3.19 (m, 2*2H, Hf), 3.72 (bs, 2H, Hg), 3.89 (t, 1H, Hh), 4.47 (dd, 2H, Hi), 4.87 and 5.00 (bs, 2*1H, Hj and Hj'), 6.90 (bs, 1H, Hk), 7.11-7.42 (m, 14H, aromatic H's). MS: (electrospray in positve mode): m/z=617 $[MH]^+$; m/z 561 $[MH]^+$-tBu; m/z=517 $[MH]^+$-boc

Example 38

N-[(2-chlorophenyl)methyl]-N'-(3,3-diphenyl-1-propyl)-N'-[2-[(piperazin-1-yl)methyl]-2-propenyl]-urea hydrochloride The operation is carried out as in Example 25 starting from the product of Example 37 instead of the product of Example 24 and in this way the expected product is obtained with a yield of 88%.

Analytical results: TLC: Rf: 0.17 (eluent: 9/1 $CH_2Cl_2$/MeOH) NMR of the hydrochloride: (DPX 300 MHz, DMSO at 80° C.): δ (ppm) 2.30 (m, 2H, Ha), 2.92 (bs, 2*2H, Hb), 3.14 (m, 2H, Hc), 3.22 (masked, 2*2H, Hd), 3.22 (masked, 2H, He), 3.94 (bs, 2H, Hf), 3.97 (t, 1H, Hg), 4.35 (bs, 2H, Hh), 5.03 and 5.23 (bs, 2*1H, Hi and Hi'), 6.69 (bs, 1H, Hj), 7.13-7.41 (m, 14H, aromatic H's), 9.23 (s, 2H, Hk). MS of the hydrochloride: m/z=517.2 $[M]^+$; m/z=551.2 $[M-2H]^-$+HCl

Example 39

(1,1-dimethylethyl) 4-[2-[[(3,3-diphenyl-1-propyl)[[(4-methoxy-phenyl)amino]carbonyl]amino]methyl]-2-propen-1-yl]-piperazinecarboxylate The operation is carried out as in Example 24 using the isocyanate 3d in Stage 3 instead of the isocyanate 3b indicated in Table 3 and in this way the expected product is obtained with a yield of 81%.

Analytical results: TLC: Rf: 0.17 (eluent: 9/1 $CH_2Cl_2$/AcOEt) NMR: (DPX 300 MHz, $CDCL_3$): δ (ppm) 1.44 (s, 9H, Ha), 2.31 (m, 2*2H, Hb), 2.38 (m, 2H, Hc), 2.94 (s, 2H, Hd), 3.19 (m, 2H, He), 3.32 (bs, 2*2H, Hf), 3.78 (s, 3H, Hg), 3.80 (s, 2H, Hh) 3.93 (t, 1H, Hi), 4.91 and 5.05 (bs, 2*1H, Hj and Hj'), 6.84 and 7.23 (AA'BB', 4H, Hk-k and Hl, l'), 7.12-7.30 (m, 10H, aromatic H's), 8.30 (bs, 1H, Hm). MS: (electrospray in positive and negative modes): m/z=599.4 $[MH]^+$; m/z=543.3 $[MH]^+$-tBu; m/z=499.3 $[MH]^+$-boc; m/z=597.4 $[M-H]^-$

Example 40

N'-(3,3-diphenyl-1-propyl)-N'-[2-[(piperazin-1-yl)methyl]-2-propen-1-yl]-N-(4-methoxyphenyl)-urea The operation is carried out as in Example 25 starting from the product of Example 39 instead of starting from the product of Example 24 and in this way the expected product is obtained with a yield of 91%.

Analytical results: TLC: Rf: 0.16 (eluent: 9/1 CH$_2$Cl$_2$/MeOH) NMR: (DPX 300 MHz, DMSO): δ (ppm) 2.16 (bs, 2*2H, Ha), 2.28 (m, 2H, Hb), 2.60 (m, 2*2H, Hc), 2.79 (bs, 2H, Hd), 3.08 (dd, 2H, He), 3.70 (s, 3H, Hf), 3.86 (bs, 2H, Hg), 3.93 (t, 1H, Hh), 4.82 and 4.97 (bs, 2*1H, Hi and Hi'), 6.81 and 7.27 (AA'BB', 4H, Hj, j' and Hk, k'), 7.16 (bt, 2H, Hl), 7.23-7.36 (m, 8H, aromatic H's), 8.41 (s, 1H, Hm). MS: m/z=499.2 [MH]$^+$; m/z=533.3 [M–H]$^-$+HCl

Example 41

N'-(3,3-diphenyl-1-propyl)-N-(4-methoxyphenyl)-N'-[2-[(piperazin-1-yl)methyl]-2-propenyl]-urea hydrochloride This salt of Example 40 is prepared by operating as in Example 26 starting from the product of Example 40 instead of the product of Example 25 and in this way the expected product is obtained with a yield of 84%.

Example 42

(1,1-dimethylethyl) 4-[2-[[(3,3-diphenyl-1-propyl)[[(4-methyl-thiophenyl)amino]carbonyl]amino]methyl]-2-propen-1-yl]-piperazinecarboxylate The operation is carried out as in Example 24 using the isocyanate 3h in Stage 3 instead of the isocyanate 3b indicated in Table 3 and in this way the expected product is obtained with a yield of 89%.

Analytical results: TLC: Rf: 0.22 (eluent: 9/1 CH$_2$Cl$_2$/AcOEt) NMR: (DPX 300 MHz, CDCl$_3$): δ (ppm) 1.45 (s, 9H, Ha), 2.33 (m, 2*2H, Hb), 2.39 (m, 2H, Hc), 2.45 (s, 3H, Hd), 2.93 (s, 2H, He), 3.20 (m, 2H, Hf), 3.37 (bs, 2*2H, Hg), 3.80 (s, 2H, Hh) 3.93 (t, 1H, Hi), 4.91 and 5.06 (bs, 2*1H, Hj and Hj'), 7.13-7.33 (m, 14H, aromatic H's), 8.28 (s, 1H, Hk). MS: (electrospray in positive and negative modes): m/z=651.3 [MH]$^+$; m/z=559.3 [MH]$^+$-tBu; m/z=515.4 [MH]$^+$-boc; m/z 613.3 [M–H]$^-$

Example 43

N'-(3,3-diphenyl-1-propyl)-N-(4-methylthiophenyl)-N'-[2-[(piperazin-1-yl)methyl]-2-propenyl]-urea hydrochloride Firstly, the operation is carried out as in Example 25 starting from the product of Example 42 instead of starting from the product of Example 24 in order to release the Nboc function to NH then the operation is carried out as in Example 26 starting from the product obtained instead of the product of Example 25 in order to prepare the expected salt. In this way the expected product is obtained with a yield of 84%.

Analytical results: TLC: Rf: 0.20 (eluent: 9/1 CH$_2$Cl$_2$/MeOH) NMR of the hydrochloride: (DPX 300 MHz, DMSO at 80° C. there is a conformational isomer 90/10): δ (ppm) 2.30 (m, 2H, Ha), 2.41 (s, 3H, Hb), 2.69 (bs, 2*2H, Hc), 3.04 (masked, 2H, Hd), 3.08 (bs, 2*2H, He), 3.19 (m, 2H, Hf), 3.97 (t, 1H, Hg), 3.97 (bs, 2H, Hh), 4.96 and 5.10 (bs, 2*1H, Hi and Hi'), 7.17 and 7.40 (AA'BB', 4H, Hj, j' and Hk, k'), 7.13-7.33 (m, 10H, aromatic H's), 8.02 (s, 1H, Hl), 8.89 (bs, 2H, Hm). MS of the hydrochloride: m/z=515.3 [M]$^+$; m/z=513.3 [M–2H]$^-$; m/z=549.3 [M–2H]$^-$+HCl

Example 44

(1,1-dimethylethyl) 4-[2-[[(3,3-diphenyl-1-propyl)[[(4-methoxy-phenyl)amino]thioxo]amino]methyl]-2-propen-1-yl]-piperazinecarboxylate The operation is carried out as in Example 24 using the isothiocyanate 3ds in Stage 3 instead of the isocyanate 3b indicated in Table 3 and in this way the expected product with a yield of 93% is obtained.

Analytical results: TLC: Rf: 0.29 (eluent: 9/1 CH$_2$Cl$_2$/AcOEt) NMR: (DPX 300 MHz, CDCl$_3$): δ (ppm) 1.41 (s, 9H, Ha), 2.31 (bs, 2*2H, Hb), 2.55 (m, 2H, Hc), 2.95 (s, 2H, Hd), 3.16 (bs, 2*2H, He), 3.68 (m, 2H, Hf), 3.81 (s, 3H, Hg), 3.95 (t, 1H, Hh), 3.98 (s, 2H, Hi), 4.78 and 5.06 (s, 2*1H, Hj and Hi'), 6.88 and 7.12 (AA'BB', 4H, Hk, k' and Hl, l'), 7.14-7.33 (m, 10H, aromatic H's), 9.88 (bs, 1H, Hm). MS: (electrospray in positive and negative modes): m/z=615.3 [MH]$^+$; m/z=559.2 [MH]$^+$-tBu; m/z=613.3 [M–H]$^-$; m/z=1227.9 [2M–H]$^-$

Example 45

N'-(3,3-diphenyl-1-propyl)-N'-[2-[(piperazin-1-yl)methyl]-2-propenyl]-N-(4-methoxyphenyl)-Thiourea hydrochloride The operation is carried out as in Example 25 starting from the product of Example 44 instead of starting from the product of Example 24 and in this way the expected product is obtained with a yield of 85%.

Analytical results: TLC: Rf: 0.27 (eluent: 9/1 CH$_2$Cl$_2$/MeOH) NMR of the hydrochloride: (DPX 300 MHz, D$_2$O at 80° C. There is a conformational isomer 90/10): δ (ppm) 2.51 (m, 2H, Ha), 3.14 (m, 2*2H, Hb), 3.35 (m, 2*2H, Hc), 3.42 (bs, 2H, Hd), 3.64 (m, 2H, He), 3.84 (s, 3H, Hf), 4.04 (t, 1H, Hg), 4.40 (bs, 2H, Hh), 5.22 and 5.37 (bs, 2*1H, Hi and Hi'), 7.01 and 7.14 (AA'BB', 4H, Hj, j' and Hk, k'), 7.22-7.45 (m, 10H aromatic H's). MS of the hydrochloride: m/z=515.3 [M]$^+$; m/z=513.3 [M–2H]$^-$; m/z=549.3 [M–2H]$^-$+HCl

Example 46

(1,1-dimethylethyl) 4-[2-[[(3,3-diphenyl-1-propyl)[[(4-phenoxy-phenyl)amino]carbonyl]amino]methyl]-2-propen-1-yl]-piperazinecarboxylate The operation is carried out as in Example 24 using the isocyanate 3l in Stage 3 instead of the isocyanate 3b indicated in Table 3 and in this way the expected product is obtained with a yield of 95%.

Analytical results: TLC: Rf: 0.23 (eluent: 9/1 CH$_2$Cl$_2$/AcOEt) NMR: (DPX 300 MHz, CDCL$_3$): δ (ppm) 1.44 (s, 9H, Ha), 2.33 (m, 2*2H, Hb), 2.39 (m, 2H, Hc), 2.95 (s, 2H, Hd), 3.20 (m, 2H, He), 3.35 (m, 2*2H, Hf), 3.81 (s, 2H, Hg), 3.93 (t, 1H, Hh) 4.92 and 5.07 (s, 2*1H, Hi and Hi'), 7.07 (bt, 1H, Hj), 6.96 and 7.31 (m, 4H+2H, Hk, k', Hl, l' and Hm), 6.96 (m, 2H, Hn), 7.12-7.34 (m, 10H, aromatic H's), 8.33 (bs, 1H, Ho). MS: (electrospray in positive and negative modes): m/z=661.3 [MH]$^+$; m/z=605.3 [MH]$^+$-tBu; m/z=659.4 [M–H]$^-$; m/z=1366.0 [2M–H]$^-$+

Example 47

N'-(3,3-diphenyl-1-propyl)-N-(4-phenoxyphenyl)-N'-[2-[(piperazin-1-yl)methyl]-2-propenyl]-urea hydrochloride The operation is carried out as in Example 25 starting from the product of Example 46 instead of starting from the product of Example 24 (release of Nboc) then the salt is prepared as in Example 26 starting from the product thus obtained instead of the product of Example 25. In this way the expected product is obtained in the form of the hydrochloride with a yield of 86%.

Analytical results: TLC: Rf: 0.23 (eluent: 9/1 $CH_2Cl_2$/MeOH) NMR of the hydrochloride: (DPX 300 MHz, DMSO at 80° C.): δ (ppm) 2.33 (m, 2H, Ha), 2.81 (bs, 2*2H, Hb), 3.10-3.50 (masked, 2*2H, Hc), 3.18 (bs, 2*2H, Hd), 3.22 (m, 2H, He), 3.99 (t, 1H, Hf), 4.03 (bs, 2H, Hg), 5.02 and 5.18 (bs, 2*1H, Hh and Hh'), 6.92 and 7.46 (AA'BB', 4H, Hi, i' and Hj, j'), 6.95 (m, 2H, Hk), 7.08 (tt, 1H, Hl), 7.17 (tt, 2H, Hm), 7.24-7.38 (m, 10H, aromatic H's), 8.08 (s, 1H, Hn), 9.09 (bs, 2H, Ho). MS of the hydrochloride: m/z=561.3 $[M]^+$; m/z=559.3 $[M-2H]^-$; m/z=595.3 $[M-2H]^-$+HCl

Example 48

(1,1-dimethylethyl) 4-[2-[[(3,3-diphenyl]-1-propyl)[[(3-methoxy-phenyl)amino]carbonyl]amino]methyl]-2-propen-1-yl]-piperazinecarboxylate The operation is carried out as in Example 24 using the isocyanate 3a in Stage 3 instead of the isocyanate 3b indicated in Table 3 and in this way the expected product is obtained with a yield of 88%.

Analytical results: TLC: Rf: 0.15 (eluent: 9/1 $CH_2Cl_2$/AcOEt) NMR: (DPX 300 MHz, $CDCl_3$): δ (ppm) 1.45 (s, 9H, Ha), 2.33 (m, 2*2H, Hb), 2.38 (m, 2H, Hc), 2.93 (bs, 2H, Hd), 3.20 (m, 2H, He), 3.39 (m, 2*2H, Hf), 3.79 (s, 3H, Hg), 3.81 (bs, 2H, Hh), 3.93 (t, 1H, Hi), 4.91 and 5.06 (s, 2*1H, Hj and Hj'), 6.58 (dd, 1H, Hk), 6.83 (dd, 1H, Hl), 7.11-7.31 (m, 12H, aromatic H's+Hm and Hn), 8.23 (bs, 1H, Ho). MS: (electrospray in positive and negative modes): m/z=599.4 $[MH]^+$; m/z=543.3 $[MH]^+$-tBu; m/z=499.3 $[MH]^+$-boc; m/z=597.4 $[M-H]^-$

Example 49

N'-(3,3-diphenyl-1-propyl)-N'-[2-[(piperazin-1-yl)methyl]-2-propen-1-yl]-N-(3-methoxyphenyl)-urea The operation is carried out as in Example 25 starting from the product of Example 48 instead of starting from the product of Example 24 and in this way the expected product is obtained with a yield of 90%.

Analytical results: TLC: Rf: 0.17 (eluent: 9/1 $CH_2Cl_2$/MeOH) NMR: (DPX 300 MHz, DMSO): δ (ppm) 2.16 (bs, 2*2H, Ha), 2.28 (m, 2H, Hb), 2.63 (m, 2*2H, Hc), 2.78 (bs, 2H, Hd), 3.10 (dd, 2H, He), 3.70 (s, 3H, Hf), 3.89 (bs, 2H, Hg), 3.94 (t, 1H, Hh), 4.82 and 4.97 (bs, 2*1H, Hi and Hi'), 6.51 (dd, 1H, Hj), 7.00 (bd, 1h, Hk), 7.08-7.19 and 7.24-7.36 (m, 12H, aromatic H's+Hl and Hm), 8.44 (s, 1H, Hn). MS: m/z=499.2 $[MH]^+$; m/z=533.3 $[M-H]^-$+HCl

Example 50

N'-(3,3-diphenyl-1-propyl)-N-(3-methoxyphenyl)-N'-[2-[(piperazin-1-yl)methyl]-2-propenyl]-urea hydrochloride The operation is carried out as in Example 26 starting from the product of Example 49 instead of the product of Example 25 and in this way the expected salt is obtained with a yield of 78%.

Example 51

(1,1-dimethylethyl)4-[2-[[[[(3,4-dimethoxyphenyl)amino]-carbonyl]-(3,3-diphenyl-1-propyl)amino]methyl]-2-propen-1-yl]-piperazinecarboxylate The operation is carried out as in Example 24 using the isocyanate 3j in Stage 3 instead of the isocyanate 3b indicated in Table 3 and in this way the expected product is obtained with a yield of 89%.

Analytical results: TLC: Rf: 0.08 (eluent: 9/1 $CH_2Cl_2$/AcOEt) NMR: (DPX 300 MHz, $CDCl_3$): δ (ppm) 1.44 (s, 9H, Ha), 2.32 (m, 2*2H, Hb), 2.39 (m, 2H, Hc), 2.94 (s, 2H, Hd), 3.20 (m, 2H, He), 3.35 (bs, 2*2H, Hf), 3.81 (s, 2H, Hg), 3.85 (s, 3H, Hh), 3.87 (s, 3H, Hi), 3.93 (t, 1H, Hj), 4.90 and 5.05 (s, 2*1H, Hk and Hk'), 6.70 (dd, 1H, Hl), 6.78 (dd, 1H, Hm), 7.18 (d, 1H, Hn), 7.13-7.32 (m, 10H, aromatic H's), 8.34 (bs, 1H, Ho). MS: (electrospray in positive and negative modes): m/z=629 $[MH]^+$; m/z=573 $[MH]^+$-tBu; m/z=529 $[MH]^+$-boc; m/z=527 $[M-H]^-$

Example 52

N'-(3,3-diphenyl-1-propyl)-N-(3,4-dimethoxyphenyl)-N'-[2-[(piperazin-1-yl)methyl]-2-propenyl]-urea hydrochloride The operation is carried out as in Example 25 starting from the product of Example 51 instead of starting from the product of Example 24 (release of Nboc) then the salt is prepared as in Example 26 starting from the product thus obtained instead of the product of Example 25. In this way the expected product is obtained in the form of the hydrochloride with a yield of 83%.

Analytical results: TLC: Rf: 0.17 (eluent: 9/1 $CH_2Cl_2$/MeOH) NMR of the hydrochloride: (DPX 300 MHz, DMSO at 80° C.): δ (ppm) 2.30 (m, 2H, Ha), 2.77 (bs, 2*2H, Hb), 3.00-3.40 (masked, 2H, Hc), 3.14 (bs, 2*2H, Hd), 3.19 (m, 2H, He), 3.70 (s, 3H, Hf), 3.72 (s, 3H, Hg), 3.97 (t, 1H, Hh), 3.99 (bs, 2H, Hi), 4.99 and 5.15 (bs, 2*1H, Hj and Hj'), 6.80 (d, 1H, Hk), 6.94 (dd, 1H, Hi), 7.11-7.19 and 7.23-7.34 (m, 11H, aromatic H's+Hm), 7.89 (s, 1H, Hn), 9.06 (bs, 2H, Ho). MS of the hydrochloride: m/z=529.3 $[M]^+$; m/z=563.3 $[M-2H]^-$+HCl

Example 53

(1,1-dimethylethyl) 4-[2-[[(3,3-diphenyl-1-propyl)[[(1,3-benzo-dioxol-4-yl)amino]carbonyl]amino]methyl]-2-propen-1-yl]-piperazinecarboxylate The operation is carried out as in Example 24 using the isocyanate 3k in Stage 3 instead of the isocyanate 3b indicated in Table 3 and in this way the expected product is obtained with a yield of 87%.

Analytical results: TLC: Rf: 0.22 (eluent: 9/1 CH$_2$Cl$_2$/AcOEt) NMR: (DPX 300 MHz, CDCL$_3$): δ (ppm) 1.44 (s, 0.9H, Ha), 2.31 (m, 2*2H, Hb), 2.37 (m, 2H, Hc), 2.93 (s, 2H, Hd), 3.18 (m, 2H He), 3.32 (m, 2*2H, Hf), 3.78 (s, 2H, Hg), 3.92 (t, 1H, Hh), 5.02 and 5.19 (bs, 2*1H, Hi and Hi'), 5.93 (s, 2H, Hj), 6.59 (dd, 1H, Hk), 3.71 (d, 1H, Hi), 7.04 (d, 1H, Hm), 7.1-7.30 (m, 10H, aromatic H's), 8.36 (bs, 1H, Hn). MS: (electrospray in positive and negative modes): m/z=613.3 [MH]$^+$; m/z=557.2 [MH]$^+$-tBu; m/z=513.2 [MH]$^+$-boc; m/z=611.4 [M–H]$^-$ Example 54

N-(1,3-benzodioxol-5-yl)-N'-(3,3-diphenyl-1-propyl)-N'-[2-[(piperazin-1-yl)methyl]-2-propenyl]-urea hydrochloride The operation is carried out as in Example 25 starting from the product of Example 53 instead of starting from the product of Example 24 (release of Nboc) then the salt is prepared as in Example 26 starting from the product thus obtained instead of the product of Example 25. In this way the expected product is obtained in the form of the hydrochloride with a yield of 79%.

Analytical results: TLC: Rf: 0.21 (eluent: 9/1 CH$_2$Cl$_2$/MeOH) NMR of the hydrochloride: (DPX 300 MHz, DMSO at 80° C.): δ (ppm) 2.30 (m, 2H, Ha), 2.86 (bs, 2*2H, Hb), 3.18 (m, 2H, Hc), 3.19 (bs, 2*2H, Hd), 3.19 (masked, 2H, He), 3.97 (t, 1H, Hf), 4.01 (bs, 2H, Hg), 5.02 and 5.19 (bs, 2*1H, Hh and Hh'), 5.91 (s, 2H, Hi), 6.73 (d, 1H, Hj), 6.82 (dd, 1H, Hk), 7.10 (d, 1H, Hi), 7.15 (tt, 2H, Hm), 7.23-7.33 (m, 8H, aromatic H's), 7.96 (bs, 1H, Hn), 9.13 (bs, 2H, Ho). MS of the hydrochloride: m/z=513.2 [M]$^+$; m/z=547.2 [M–2H]$^-$+HCl Example 55

(1,1-dimethylethyl) 4-[2-[[(3,3-diphenyl-1-propyl)[[(3,4,5-trimehoxyphenyl)amino]carbonyl]amino]methyl]-2-propen-1-yl]-piperazinecarboxylate The operation is carried out as in Example 24 using the isocyanate 3l in Stage 3 instead of the isocyanate 3b indicated in Table 3 and in this way the expected product is obtained with a yield of 94%.

Analytical results: TLC: Rf: 0.07 (eluent: 9/1 CH$_2$Cl$_2$/AcOEt) NMR: (DPX 300 MHz, CDCl$_3$): δ (ppm) 1.44 (s, 9H, Ha), 2.35 (m, 2*2H, Hb), 2.38 (m, 2H, Hc), 2.95 (bs, 2H, Hd), 3.19 (m, 2H, He), 3.41 (bs, 2*2H, Hf), 3.81 (s, 3H, Hg), 3.82 (s, 2*3H, Hh), 3.82 (bs, 2H, Hi), 3.93 (t, 1H, Hj), 4.90 and 5.07 (s, 2*1H, Hk and Hk'), 6.68 (bs, 2H, Hi), 7.12-7.32 (m, 10H, aromatic H's), 8.39 (bs, 1H, Hm). MS: (electrospray in positive and negative modes): m/z=659.3 [MH]$^+$; m/z=603.3 [MH]$^+$-tBu; m/z=559.2 [MH]$^+$-boc; m/z=657.4 [M–H]$^-$ Example 56

N'-(3,3-diphenyl-1-propyl)-N'-[2-[(piperazin-1-yl)methyl]-2-propenyl]-N-(3,4,5-trime-thoxyphenyl)-urea hydrochloride The operation is carried out as in Example 25 starting from the product of Example 55 instead of starting from the product of Example 24 (release of Nboc) then the salt is prepared as in Example 26 starting from the product thus obtained instead of the product of Example 25. In this way the expected product is obtained in the form of the hydrochloride with a yield of 86%.

Analytical results: TLC: Rf: 0.16 (eluent: 9/1 CH$_2$Cl$_2$/MeOH) NMR of the hydrochloride: (DPX 300 MHz, DMSO at 80° C.): δ (ppm) 2.30 (m, 2H, Ha), 2.77 (bs, 2*2H, Hb), 3.07-3.39 (masked, 2H, Hc), 3.14 (bs, 2*2H, Hd), 3.19 (m, 2H, He), 3.62 (s, 3H, Hf), 3.73 (s, 2*3H, Hg), 3.97 (t, 1H, Hh), 4.00 (bs, 2H, Hi), 4.99 and 5.14 (bs, 2*1H, Hj and Hj'), 6.86 (s, 2H, Hk), 7.11-7.34 (m, 10H, aromatic H's), 7.93 (s, 1H, Hl), 7.89 (s, 1H, Hn), 9.02 (bs, 2H, Hm). MS of the hydrochloride: m/z=559.3 [M]$^+$; m/z=693.2 (M–2H]-+HCl Example 57

(1,1-dimethylethyl) 4-[2-[[(3,3-diphenyl-1-propyl)[[[4-(trifluoromethyl)phenyl]amino]carbonyl]amino]methyl]-2-propen-1-yl]-piperazinecarboxylate The operation is carried out as in Example 24 using the isocyanate 3m in Stage 3 instead of the isocyanate 3b indicated in Table 3 and in this way the expected product is obtained with a yield of 95%.

Analytical results: TLC: Rf: 0.20 (eluent: 9/1 CH$_2$Cl$_2$/AcOEt) NMR: (DPX 300 MHz, CDCL$_3$, there is a conformational isomer 90/10): δ (ppm) 1.47 (s, 9H, Ha), 2.35 (m, 2*2H, Hb), 2.39 (m, 2H, Hc), 2.94 (bs, 2H, Hd), 3.21 (m, 2H, He), 3.40 (bs, 2*2H, Hf), 3.82 (bs, 2H, Hg), 3.94 (t, 1H, Hh), 4.93 and 5.01 (bs, 2*1H, Hi and Hi'), 7.13-7.32 (m, 10H, aromatic H's), 7.49 and 7.52 (AA'BB', 4H, and Hj, j' Hk, k'), 8.42 (s, 1H, Hl). MS: (electrospray in positive and negative modes): m/z=637.3 [MH]$^+$; m/z=681.2 [MH]$^+$-tBu; m/z=635.3 [M–H]$^-$; m/z=1271.9 [2M–H]$^-$ Example 58

N'-(3,3-diphenyl-1-propyl)-N-[4-(trifluoromethyl)phenyl]-N'-[2-[(piperazin-1-yl)methyl]-2-propenyl]-urea hydrochloride The operation is carried out as in Example 25 starting from the product of Example 57 instead of starting from the product of Example 24 (release of Nboc) then the salt is prepared as in Example 26 starting from the product thus obtained instead of the product of Example 25. In this way the expected product is obtained in the form of the hydrochloride with a yield of 84%.

Analytical results: TLC: Rf: 0.17 (eluent: 9/1 CH$_2$Cl$_2$/MeOH) NMR of the hydrochloride: (DPX 300 MHz, DMSO at 80° C. there is a conformational isomer 90/10): δ (ppm) 2.32 (m, 2H, Ha), 2.77 (bs, 2*2H, Hb), 3.15 (bs, 2*2H, Hc), 3.23 (m, 2H, Hd), 3.00-3.60 (masked, 2H, He), 3.98 (t, 1H, Hf), 4.06 (bs, 2H, Hg), 4.96 and 5.10 (bs, 2*1H, Hh and Hh'), 7.12-7.33 (m, 10H, aromatic H's), 7.53 and 7.68 (AA'BB', 4H, and Hi, i' Hj, j'), 8.49 (s, 1H, Hk), 8.89 (bs, 2H, Hl). MS of the hydrochloride: m/z=537.3 [M]$^+$; m/z=635.3 [M–2H]$^-$; m/z=571.2 [M–2H]$^-$+HCl

Example 59

N-(3,3-diphenyl-1-propyl)-N-(2-methylpropyl)-N'-(4-methylphenyl)-urea

Stage 1: Synthesis of Compound (19)

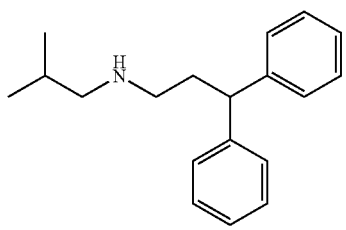

(19)

3,3-diphenylpropylamine (20) (2.00 g, 9.53 mmol, 1 eq) and isobutyraldehyde (21) (682 mg, 9.46 mmol, 1 eq) in 50 ml of methanol are introduced successively into a 50 mL flask under a nitrogen atmosphere. The reaction medium is then stirred for 45 minutes at ambient temperature before introducing NaBH$_3$CN (595 mg, 9.47 mmol, 1 eq). Once this introduction has been carried out, the stirring is continued for 24 hours. The reaction medium is then taken up in water, and the organic phase is extracted with dichloromethane. The latter is dried over MgSO$_4$, filtered and the solvent is driven off under vacuum using a rotary evaporator. The yellow oil obtained is then chromatographed on a silica column (eluent: 60/40 CH$_2$Cl$_2$/AcOEt) in order to finally obtain the expected product (19) also in the form of a yellow oil (1.18 g, η=46%).

Analytical results: TLC: Rf: 0.27 (eluent: 9/1 CH$_2$Cl$_2$/MeOH) NMR: (DPX 300 MHz, CDCL3): δ (ppm) 0.73 (d, 2*3H, Ha), 1.59 (septuplet, 1H, Hb), 2.13 (q, 2H, Hc), 2.27 (d, 2H, Hd), 2.45 (t, 2H, He), 3.90 (t, 1H, Hf), 7.00-7.20 (m, 10H, aromatic H's).

Stage 2: N-(3,3-diphenyl-1-propyl)-N-(2-methylpropyl)-N'-(4-methylphenyl)-urea

The operation is carried out as in Stage 3 of Example 24 starting from the product obtained in Stage 1 above instead of the product obtained in Stage 2 of Example 24 using the isocyanate 3g instead of the isocyanate 3b indicated in Table 3. In this way the expected product is obtained with a yield of 94%.

Example 60

N-(3,3-diphenyl-1-propyl)-N-(2-methylpropyl)-N'-[(2-chlorophenyl)methyl]-urea

The operation is carried out as in Stage 2 of Example 59 using the isocyanate 3e instead of the isocyanate 3g and in this way the expected product is obtained with a yield of 91%.

Example 61

N-(3,3-diphenyl-1-propyl)-N-(2-methylpropyl)-N'-(3-methoxyphenyl)-urea

The operation is carried out as in Stage 2 of Example 59 using the isocyanate 3a instead of the isocyanate 3g and in this way the expected product is obtained with a yield of 90%.

Example 61b

N-(3,3-diphenyl-1-propyl)-N-(2-methylpropyl)-N'-(4-methoxyphenyl)-urea

The operation is carried out as in Stage 2 of Example 59 using the isocyanate 3d instead of the isocyanate 3g and in this way the expected product is obtained with a yield of 85%.

Analytical results: TLC: Rf: 0.82 (eluent: 9/1 CH$_2$Cl$_2$/MeOH) NMR: (DPX 300 MHz, CDCL3): δ (ppm) 0.89 (d, 2*3H, Ha), 1.91 (m, 1H, Hb), 2.40 (m, 2H, Hc), 3.08 (d, 2H, Hd), 3.23 (m, 2H, He), 3.77 (s, 3H, Hf)), 3.91 (bt, 1H, Hg), 5.98 (bs, 1H, Hh); 6.80 and 7.15 (AA'BB', 4H, Hi, i',j, j'), 7.16-7.36 (m, 10H, aromatic H's). MS: (electrospray in positive mode): m/z=417 [MH]$^+$; m/z=437 [MNa]$^+$; m/z=833 [2M+H]$^+$

Example 62 methyl 3-[[[(3,3-diphenyl-1-propyl)(2-methylpropyl)-amino]carbonyl]amino]-benzoate The operation is carried out as in Stage 2 of Example 59 using the isocyanate 3b instead of the isocyanate 3g and in this way the expected product is obtained with a yield of 91%.

Analytical results: TLC: Rf: 0.86 (eluent: 9/1 CH$_2$Cl$_2$/MeOH) NMR: (DPX 300 MHz, CDCL3): δ (ppm) 0.91 (d, 2*3H, Ha), 1.93 (m, 1H, Hb), 2.42 (m, 2H, Hc), 3.11 (d, 2H, Hd), 3.26 (dd, 2H, He), 3.92 (masked, 1H, Hf), 3.92 (s, 3H, Hg), 6.08 (s, 1H, Hh), 7.19-7.38 and 7.69 (m, 11H and 3H, aromatic H's). MS: (electrospray in positive mode): m/z=445 [MH]$^+$; m/z=413 [MH]$^+$-MeOH; m/z=467 [MNa]$^+$

Example 63

3-[[[(3,3-diphenyl-1-propyl)(2-methylpropyl)-amino]carbonyl]amino]benzoic acid

The operation is carried out as in Example 27 starting from the product obtained in Example 62 and in this way the expected product is obtained with a yield of 69%.

Example 64

N'-(3,3-diphenyl-1-propyl)-N'-(2-methyl-propyl)-N-(1,3-benzodioxol-5-yl)-urea

The operation is carried out as in Stage 2 of Example 59 using the isocyanate 3k instead of the isocyanate 3g and in this way the expected product is obtained with a yield of 92%.

Example 65

N'-(3,3-diphenyl-1-propyl)-N'-(2-methyl-propyl)-N-(3,4-dimethoxyphenyl)-urea

The operation is carried out as in Stage 2 of Example 59 using the isocyanate 3j instead of the isocyanate 3g and in this way the expected product is obtained with a yield of 89%.

Example 66

N'-(3,3-diphenyl-1-propyl)-N'-(2-methyl-1-propyl)-N-(3,4,5-trimethoxyphenyl)-urea hydrochloride The operation is carried out as in Stage 2 of Example 59 using the isocyanate 3l instead of the isocyanate 3g and in this way the expected product is obtained with a yield of 94%.

Example 67

N'-(3,3-diphenyl-1-propyl)-N'-(2-methyl-propyl)-N-(4-phenoxyphenyl)-urea

The operation is carried out as in Stage 2 of Example 59 using the isocyanate 3l instead of the isocyanate 3g and in this way the expected product is obtained with a yield of 88%.

Example 68

N'-(3,3-diphenyl-1-propyl)-N'-(2-methyl-propyl)-N-[4-(trifluoromethyl)-phenyl]-urea The operation is carried out as in Stage 2 of Example 59 using the isocyanate 3m instead of the isocyanate 3g and in this way the expected product is obtained with a yield of 87%.

Example 69

N'-(3,3-diphenyl-1-propyl)-N'-(2-methyl-propyl)-N-[(4-methoxyphenyl)methyl]-urea The operation is carried out as in Stage 2 of Example 59 using the isocyanate 3n instead of the isocyanate 3g and in this way the expected product is obtained with a yield of 93%.

Example 70

N'-(3,3-diphenyl-1-propyl)-N'-(2-methyl-propyl)-N-(phenylethyl)-urea

The operation is carried out as in Stage 2 of Example 59 using the isocyanate 3c instead of the isocyanate 3g and in this way the expected product is obtained with a yield of 85%.

Example 71

N'-(3,3-diphenyl-1-propyl)-N'-(2-methyl-propyl)-N-cyclohexyl-urea

The operation is carried out as in Stage 2 of Example 59 using the isocyanate 3c instead of the isocyanate 3g and in this way the expected product is obtained with a yield of 86%.

Example 72

N'-(3,3-diphenyl-1-propyl]-N'-(2-methyl-propyl)-N-(tricyclo[3.3.1.13.7]dec-1-yl)-urea The operation is carried out as in Stage 2 of Example 59 using the isocyanate 3p instead of the isocyanate 3g and in this way the expected product is obtained with a yield of 83%.

Example 73

N'-(3,3-diphenyl-1-propyl)-N'-(2-methylpropyl)-N-(4-butoxyphenyl)-urea

The operation is carried out as in Stage 2 of Example 59 using the isocyanate 3q instead of the isocyanate 3g and in this way the expected product is obtained with a yield of 86%.

Example 131

Pharmaceutical Composition

Tablets were prepared corresponding to the following formula:
Product of Example 24 . . . 0.2 g
Excipient for a tablet completed at . . . 1 g
(detail of excipient: lactose, talc, starch, magnesium stearate).

The invention claimed is:
1. A compound of Formula I

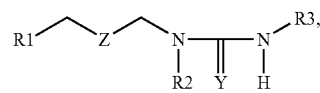

or a pharmaceutically acceptable salt thereof, wherein:
Y is an oxygen or sulphur atom,
Z is —C(=CH$_2$)—, —CH(CH$_3$)—
$R^1$ is an optionally substituted morpholinyl radical or a saturated diamine radical of formula:

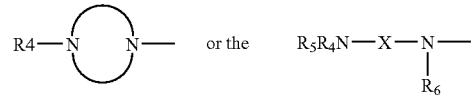

radical,
wherein the continuous arc indicates that the two nitrogen atoms form a monocyclic, heterocyclic, saturated, optionally substituted radical constituted by at most 8 members, the nitrogen atoms optionally being consecutive on the ring thus formed;
X is a linear or branched alkylene radical containing at most 6 carbon atoms;
$R^4$ is the hydrogen atom, an esterified carboxy radical, or an optionally substituted linear or branched alkyl radical containing at most 4 carbon atoms;
$R^5$ and $R^6$, which could be identical or different, are the hydrogen atom, an optionally substituted linear or branched alkyl radical containing at most 4 carbon atoms;
$R^2$ is a linear or branched alkyl radical containing at most 6 atoms substituted by one or more identical or different radicals chosen from the aryl or heteroaryl radicals themselves optionally substituted;
$R^3$ is a linear or branched alkyl radical containing at most 6 carbon atoms, cycloalkyl containing at most 12 members, aryl, heteroaryl, arylalkyl or heteroarylalkyl in which the alkyl radical is linear or branched containing at most 4 carbon atoms, all these radicals being optionally substituted.

2. The compound or salt of claim 1, wherein Y is oxygen.

3. The compound or salt of claim 1, wherein Y is sulfur.

4. The compound or salt of claim 1, wherein $R^1$ is morpholinyl, piperazinyl, methylpiperazinyl, or 1,4 diazepanyl.

5. The compound or salt of claim 1, wherein $R^1$ is the

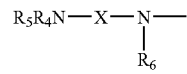

radical, wherein X is a carbonyl, or linear or branched alkylene radical containing at most 4 carbon atoms;
R4, R5 and R6, which could be identical or different are the hydrogen atom, an optionally substituted liner or branched alkyl radical containing at most 4 carbon atoms, an optionally substituted cycloalkyl radical containing at most 6 members, an optionally substituted aryl radical, or an optionally substituted arylalkyl radical.

6. The compound or salt of claim 5, wherein X is methylenyl or ethylenyl.

7. The compound or salt of claim 5, wherein R6 is methyl.

8. The compound or salt of claim 5, wherein R4 is hydrogen or methyl.

9. The compound or salt of claim 5, wherein R5 is hydrogen or methyl.

10. The compound or salt of claim 1, wherein $R^3$ is aryl, heteroaryl, arylalkyl or heteroarylalkyl in which the alkyl radical is linear or branched containing at most 4 carbon atoms, all these radicals being optionally substituted.

11. The compound or salt of claim 10, wherein $R^3$ is aphenyl radical, wherein the phenyl radical is optionally substituted by one or more identical or different radicals chosen front the phenyl, methoxy, trifluoromethyl, free, salified or esterified carboxy radicals, the linear or branched alkyl, alkenyl, alkylthio and alkoxy radicals containing at most 4 carbon atoms and the —NH$_2$ radical in which the hydrogen atoms are optionally substituted by one or two linear or branched alkyl radicals containing at most 4 carbon atoms.

12. The compound or salt of claim 1, wherein Z is —C(=CH$_2$)—.

13. The compound or salt of claim 1, wherein Z is —CH(CH$_3$)—.

14. The compound or salt of claim 1, wherein $R^2$ diphenyipropyl.

15. The compound, or a pharmaceutically acceptable salt thereof according to claim 1, wherein the compound is selected from the group consisting of:
methyl 3-(3-(3,3-diphenylpropyl)-3-(3-(4-methylpiperazin-1-yl)propyl)ureido)benzoate,
methyl 2-chloro-5-(3-(3,3-diphenylpropyl)-3-(3-(4-methylpiperazin-1-yl)propyl)ureido)benzoate,
methyl 3-(3-(3,3-diphenylpropyl)-3-(3-morpholinopropyl)ureido)benzoate,
1-(2-((1,4-diazepan-1-yl)methyl)allyl)-1-(3,3-diphenylpropyl)-3-(3-methoxyphenyl)urea,
methyl 3-(3-(2-((1,4-diazepan-1-yl)methyl)allyl)-3-(3,3-diphenylpropyl)ureido)benzoate,
4-(4-(2-(1-(3,3-diphenylpropyl)-3-m-tolylureido)methyl)allyl)piperazin-1-yl)-4-oxobutanoic acid,
tert-butyl 4-(3-(1-(3,3-diphenylpropyl)-3-(3-(methoxycarbonyl)phenyl)ureido)propyl)piperazine-1-carboxylate,
phenyl 4-(3-(1-(3,3-diphenylpropyl)-3-(3-(methoxycarbonyl)phenyl)ureido)propyl)piperazine-1-carboxylate,
1-(3,3-diphenylpropyl)-1-(3-morpholinopropyl)-3-(3-propionylphenyl)urea,
methyl 3-(3-(3,3-diphenylpropyl)-3-(2-(piperazin-1-yl)methyl)allyl)ureido)benzoate,
1-(3,3-diphenylpropyl)-1-(2-(piperazin-1-ylmethyl)allyl)-3-m-tolylurea,
methyl 3-(3-(3,3-diphenylpropyl)-3-(2-((4-metbylpiperrzin-1-yl)methyl)allyl)ureido)benzoate,
isopropyl 4-(3-(1-(3,3-diphenylpropyl)-3-(3-(methoxycarbonyl)phenyl)ureido)propyl)piperazine-1-carboxylate,
1-(3,3-diphenylpropyl)-3-(3-(methylthio)phenyl)-1-(3-morpholinopropyl)urea,
3-(3-chlorophenyl)-1-(3,3-diphenylpropyl)-1-(2-(piperazin-1-ylmethyl)allyl)urea,
1-(3,3-diphenylpropyl)-1-(2-((4-methylpiperazin-1-yl)methyl)allyl)-3-m-tolylurea,
methyl 3-(3-(3,3-diphenylpropyl)-3-(2-methyl-3-(piperazin-1-yl)propyl)ureido)benzoate,
1-(2-((1,4-diazepan-1-yl)methyl)allyl)-3-(3-chlorophenyl)-1-(3,3-diphenylpropyl)urea,
methyl 3-(3-(3,3-diphenylpropyl)-3-(2-((methyl(3-(methylamino)propyl)amino)methyl)allyl)ureido)benzoate,
methyl 4-(3-(1-(3,3-diphenylpropyl)-3-(3-(methoxycarbonyl)phenyl)ureido)propyl)piperazine-1-carboxylate,
allyl 4-(3-(1-(3,3-diphenylpropyl)-3-(3-(methoxycarbonyl)phenyl)ureido)propyl)piperazine-1-carboxylate,
1-(3,3-diphenylpropyl)-3-(3-methoxyphenyl)-1-(2-(piperazin-1-ylmethyl)allyl)urea,
1-(3,3-diphenyipropyl)-1-(2-methyl-3-(piperazin-1-yl)propyl)-3-p-tolylurea,
methyl 3-(3-(3,3-diphenylpropyl)-3-(2-((methyl(2-(methylamino)ethyl)amino)methyl)allyl)ureido)benzoate,
1-(3,3-diphenylpropyl)-1-(2-((methyl-3-(methylamino)propyl)amino)methyl))allyl)-3-m-tolylurea,
1-(3,3-diphenylpropyl)-3-(3-methoxyphenyl)-1-(2-((methyl(3-(methylamino)propyl)amino)methyl)allyl)urea,
tert-butyl 4-(2-((1-(3,3-diphenylpropyl)-3-(3-(methoxycarbonyl)phenyl)ureido)methyl)allyl)piperazine-1-carboxylate,
tert-butyl 4-(2-((1-(3,3-diphenylpropyl)-3-p-tolylureido)methyl)allyl)piperazine-1-carboxylate,
1-(3,3-diphenylpropyl)-3-(3-methoxyphenyl)-1-(2-((methyl(2-(methylamino)ethyl)amino)methyl)allyl)urea,
1-(3,3-diphenylpropyl)-1-(2-(piperazin-1-ylmethyl)allyl)-3-(2-(thiophen-2-yl)ethyl)urea,
1-(3,3-diphenylpropyl)-1-(2-((methyl(2-(methylamino)ethyl)amino)methyl)allyl)-3-p-tolylurea,
1-(3,3-diphenylpropyl)-1-2-((methyl(3-(methylamino)propyl)amino)methyl)allyl)-3-phenylurea,
1-(3,3-diphenylpropyl)-3-(4-methoxyphenyl)-1-(2-((methyl(3-(methylamino)propyl)amino)methyl)allyl)urea,
1-(3,3-diphenylpropyl)-3-(4-methoxyphenyl)-1-(2-(piperazin-1-ylmethyl)allyl)urea,
1-(3,3-diphenylpropyl)-3-(3-methoxyphenyl)-1-(2-(piperazin-1-ylmethyl)allyl)urea,
1-(3,3-diphenylpropyl)-1-(2-(piperazin-1-ylmethyl)allyl)-3-p-tolylurea,
3-(3,4-dimethoxyphenyl)-1-(3,3-diphenylpropyl)-1-(2-(piperazin-1-ylmethyl)allyl)urea,
1-(3,3-diphenylpropyl)-1-(2-(piperazin-1-ylmethyl)allyl)-3-(4-(trifluoromethyl)phenyl)urea, and
1-(3,3-diphenyipropyl)-1-(2-(piperazin-1-ylmethyl)allyl)-3-(3,4,5-trimethoxyphenyl)urea.

16. A pharmaceutical composition comprising a compound of Formula I, or a pharmaceutically acceptable salt thereof, and a pharmaceutically acceptable diluent or carrier

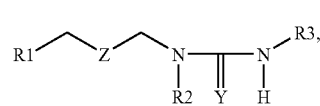

wherein:
wherein:
Y is an oxygen or sulphur atom,
Z is —C(=CH$_2$)—, —CH(CH$_3$)—
$R^1$ is an optionally substituted morpholinyl radical or a saturated diamine radical of formula:

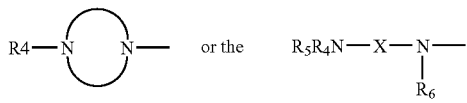

radical,
wherein the continuous arc indicates that the two nitrogen atoms form a monocyclic, heterocyclic, saturated, optionally substituted radical constituted by at most 8 members, the nitrogen atoms optionally being consecutive on the ring thus formed;

X is a linear or branched alkylene radical containing at most 6 carbon atoms;

$R^4$ is the hydrogen atom, an esterified carboxy radical, or an optionally substituted linear or branched alkyl radical containing at most 4 carbon atoms;, $R^5$ and $R^6$ which could be identical or different, are the hydrogen atom, an optionally substituted linear or branched alkyl radical containing at most 4 carbon atom;

$R^2$ is a linear or branched alkyl radical containing at most 6 carbon atoms substituted by one or more identical or different radicals chosen from the aryl or heteroaryl radicals themselves optionally substituted;

$R^3$ is a linear or branched alkyl radical containing at most 6 carbon atoms, cycloalkyl containing at most 12 members, aryl, heteroaryl, arylailcyl or heteroarylalkyl in which the alkyl radical is linear or branched containing at most 4 carbon atoms, all these radicals being optionally substituted.

17. A pharmaceutical composition comprising the compound or salt of claim 14 and a pharmaceutically acceptable diluent or carrier.

18. A pharmaceutical composition comprising the compound or salt of claim 15 and a pharmaceutically acceptable diluent or carrier.

19. A method of treating hyperparathyroidism comprising administering to a patient in need thereof a compound of Formula I

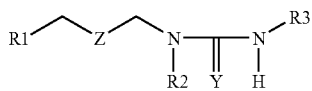

or a pharmaceutically acceptable salt thereof, wherein:
Y is an oxygen or sulphur atom,
Z is —C(=CH$_2$)—, —CH(CH$_3$)— or —CH$_2$—;

$R^1$ is an optionally substituted morpholinyl radical or a saturated diamine radical of formula:

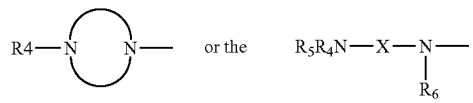

radical
wherein the continuous are indicates that the two nitrogen atom form a monoeyelic heteroeyelic, saturated, optionally substituted radical constituted by at most 8 member, the nitrogen atom optionally being consecutive on the ring thus formed;

X is a carbonyl, or linear or branched alkylene radical containing at most 6 carbon atoms;

R4, R5 and R6, which could be identical or different, are the hydrogen atom, an esterified carboxy radical, a benzyl radical, an optionally substituted linear or branched alkyl radical containing at most 4 carbon atoms, an optionally substituted cycloalkyl radical containing at most 6 member, an optionally substituted aryl radical, or an optionally substituted arylalkyl radical;

R2 is a linear or branched alkyl radical containing at most 6 carbon atoms substituted by one or more identical or different radical chosen from the aryl or heteroaryl radicals themselves optionally substituted;

R3 is a linear or branched alkyl radical containing at most 6 carbon atoms, cycloalkyl containing at most 12 members, aryl, heteroaryl, arylalkyl or, heteroarylalkyl in which the alkyl radical is linear or branched cantaining at most 4 carbon atoms, all the radicals being optionally substituted.

20. The method of claim 19, wherein hyperthyroidism is primary hyperthyroidism.

21. The method of claim 19, wherein hyperthyroidism is secondary hyperthyroidism.

22. A method of treating hyperparathyroidism comprising administering to a patient in need thereof a compound or pharmaceutically acceptable salt thereof according to claim 15.

23. A method of treating hypocalcaemia comprising administering to a patient in need thereof a compound or pharmaceutically acceptable salt thereof according to claim 1 or claim 15.

* * * * *